(12) United States Patent
Belcher et al.

(10) Patent No.: US 10,521,433 B2
(45) Date of Patent: Dec. 31, 2019

(54) DOMAIN SPECIFIC LANGUAGE TO QUERY MEDICAL DATA

(71) Applicant: RADICALOGIC TECHNOLOGIES, INC., Toronto (CA)

(72) Inventors: Thomas Belcher, Northgate (AU); Simon McKenna, Bellevue Heights (AU)

(73) Assignee: RLDATIX NORTH AMERICA INC., Toronto (CA)

( * ) Notice: Subject to any disclaimer, the term of this patent is extended or adjusted under 35 U.S.C. 154(b) by 196 days.

(21) Appl. No.: 15/816,533

(22) Filed: Nov. 17, 2017

(65) Prior Publication Data
US 2018/0137177 A1 May 17, 2018

Related U.S. Application Data

(60) Provisional application No. 62/423,429, filed on Nov. 17, 2016.

(51) Int. Cl.
*G06F 16/20* (2019.01)
*G06F 16/2457* (2019.01)
(Continued)

(52) U.S. Cl.
CPC ...... *G06F 16/2457* (2019.01); *G06F 16/2433* (2019.01); *G16H 10/60* (2018.01); *G16H 50/70* (2018.01)

(58) Field of Classification Search
None
See application file for complete search history.

(56) References Cited

U.S. PATENT DOCUMENTS

| 6,263,342 B1 * | 7/2001 | Chang | G06F 16/2452 |
| 2003/0227487 A1 * | 12/2003 | Hugh | G06F 16/9024 715/777 |

(Continued)

OTHER PUBLICATIONS

Barišić et al., Patterns for Evaluating Usability of Domain-Specific Languages, Proceedings of the 19th Conference on Pattern Languages of Programs, Oct. 19-21, 2012, p. 1-34, Tucson, Arizona.

*Primary Examiner* — Jau Shya Meng
(74) *Attorney, Agent, or Firm* — Norton Rose Fulbright Canada LLP

(57) ABSTRACT

A query device for conducting automated user identification using a domain specific query language is described. The domain specific language is a computer language specially adapted for use in the healthcare domain. The domain specific language includes specific syntax suitable to the medical or healthcare industries, and is structured in the form of a string for processing. The domain-specific query is automatically processed and delineated into one or more processing sections. The domain-specific query is specifically structured for improved efficiency through iterative processing of the one or more processing sections, where each of the one or more processing sections is classified and mapped to a specific filter. Each filter represents a programmatic mechanism for automatically conducting a query against one or more backend data storages or other datasets to return a list of users or equipment that meet the criteria of the filter. Corresponding methods, and computer readable media are described.

20 Claims, 22 Drawing Sheets

(51) Int. Cl.
*G06F 16/242* (2019.01)
*G16H 10/60* (2018.01)
*G16H 50/70* (2018.01)

(56) References Cited

U.S. PATENT DOCUMENTS

| | | | | |
|---|---|---|---|---|
| 2013/0275164 A1* | 10/2013 | Gruber | ................... | G10L 17/22 |
| | | | | 705/5 |
| 2014/0075004 A1* | 3/2014 | Van Dusen | ............. | H04L 41/04 |
| | | | | 709/223 |
| 2016/0034463 A1* | 2/2016 | Brewer | .............. | G06F 16/9024 |
| | | | | 707/734 |

* cited by examiner

Software for safer healthcare

Patient Search

MENU

Organism identifier
VRE = Vancomycoin Reseasistant Enderbooccus

Ward, station or clinic where patient is being accommodated or treated

ICU = Intensive Care Unit
NICU = Neonatal Intensive Care Unit any current inpatients with isolate "VRE" in unit "ICU" for more than 2 weeks

 Create alert

Alert properties

| General | Message | Content | | Schedules | ? |

Alert Type: Surveillance Alert
Alert Definition: any current inpatients with isolate "VRE" in unit "ICU" or "NICU" for more than 2 weeks.

 Creation of an Alert on Infection Surveillance Search Page
5000

FIG. 8

```
/// <summary>
/// Matches:
/// (,) (and) (is|being) (not) on [antiinfective|antibiotic] (`(Antiinfective)` (or `...`))
/// (in [class|group] `(Class)` (or `...`)) (delivered (via) `(Method)`)
/// (at [facility|unit|building|floor|room|bed|icu|neonatal] (`(Location)` (or `...`)))
/// </summary>
public static readonly Parser<AntiinfectiveFilter> AntiinfectiveSection =
    from separator in Lexicon.SectionDelimiter.Optional()
    from isBeing in Lexicon.Is.Or(Lexicon.Being).Optional()
    from invert in Parse.WhiteSpace.Optional()
    from antiinfective in Parse.WhiteSpace.Optional()      ← Unique keyword(s) to identify section
        .Then(match => Lexicon.Not)
        .Select(match => true).Optional()
        .Then(match => Lexicon.On).Optional()
        .Then(match => Lexicon.Antibiotic.Or(Lexicon.Antiinfective))
        .Then(match => Lexicon.QuotedTextMany.Optional()
    from classes in Parse.WhiteSpace.Optional()
        .Then(match => Lexicon.In).Optional()              ← Optional parameters which can be shared
        .Then(match => Lexicon.Class.Or(Lexicon.Group).Optional()     and re-used between different sections
        .Then(match => Lexicon.QuotedTextMany).Optional()
    from methods in Parse.WhiteSpace.Optional()
        .Then(match => Lexicon.Delivered).Optional()
        .Then(match => Lexicon.Via).Optional()
        .Then(match => Lexicon.QuotedTextMany).Optional()
    from location in Lexicon.LocatedAt.Optional()          ← instantiates associated filter when parsed
    select new AntiinfectiveFilter(
        invert.GetOrDefault(),
        antiinfectives.GetOrDefault(),
        classes.GetOrDefault(),
        methods.GetOrDefault(),
        location.GetOrDefault());
```

FIG. 15

```
public static class Lexicon
{
    #region Single Words
    public static readonly Parser<string>
        A = Parse.IgnoreCase("a").Text().Token();
    public static readonly Parser<string>
        Admission = Parse.IgnoreCase("admission").Text().Token();
    public static readonly Parser<string>
        Admitted = Parse.IgnoreCase("admitted").Text().Token();
    public static readonly Parser<string>
        After = Parse.IgnoreCase("after").Text().Token();
    public static readonly Parser<string>
        An = Parse.IgnoreCase("an").Text().Token();
    public static readonly Parser<string>
        Antibiotic = Parse.IgnoreCase("antibiotic").Text().Token();
    public static readonly Parser<string>
        Antiinfective = Parse.IgnoreCase("antiinfective").Text().Token();
```

FIG. 16

```
#region Combined Words
public static readonly Parser<string>
    AtLeast = At.Then(c => Least);
public static readonly Parser<string>
    AtMost = At.Then(c => Most);
public static readonly Parser<bool>
    DoesNotHave = Does
        .Then(match => Not)
        .Then(match => Have)
        .Select(match => true);
public static readonly Parser<string>
    EqualTo = Equal.Then(c => To);
public static readonly Parser<bool>
    InIsolation = In
        .Then(match => Isolation)
        .Select(match => true);
public static readonly Parser<bool>
    InSpecialty = In.Optional()
        .Then(match => Specialty)
        .Select(match => true);
```

FIG. 17

```
#region Enumerations
public static readonly Parser<CompareNumberEnum>
    CompareAge = Older.Then(match => Than).Return(CompareNumberEnum.GreaterThan)
        .Or(Younger.Then(match => Than).Return(CompareNumberEnum.LessThan));
public static readonly Parser<CompareNumberEnum>
    CompareInequality = AtLeast.Return(CompareNumberEnum.GreaterThanOrEqualTo)
        .Or(AtMost.Return(CompareNumberEnum.LessThanOrEqualTo))
        .Or(MoreThan.Return(CompareNumberEnum.GreaterThan))
        .Or(LessThan.Return(CompareNumberEnum.LessThan))
        .Or(EqualTo.Return(CompareNumberEnum.EqualTo))
        .Or(Within.Return(CompareNumberEnum.Between));
public static readonly Parser<CompareTimeEnum>
    CompareTime = After.Return(CompareTimeEnum.After)
        .Or(Before.Return(CompareTimeEnum.Before))
        .Or(During.Return(CompareTimeEnum.During));
public static readonly Parser<CompareTimeEnum>
    CompareTimeFromNow = Next.Return(CompareTimeEnum.After)
        .Or(Last.Return(CompareTimeEnum.Before));
```

FIG. 18

```
public static class Grammar
{
    /// <summary>
    /// Matches:
    /// (,) (and) (not) [admitted|admission|readmitted|readmission] (from '{Source}' (or '...'))
    /// </summary>
    public static readonly Parser<AdmissionFilter> AdmissionSection =
        from separator in Lexicon.SectionDelimiter.Optional()
        from not in Lexicon.Not.Select(match => true).Optional()
        from readmitted in Lexicon.Admitted
            .Or(Lexicon.Admission).Select(match => false)
            .Or(Lexicon.Readmitted).Or(Lexicon.Readmission).Select(match => true))
        from source in Lexicon.From.Then(match => Lexicon.QuotedTextMany).Optional()
        select new AdmissionFilter(
            not.GetOrDefault(),
            source.GetOrDefault(),
            readmitted);
}
```

FIG. 19

```
public InfectionFilterResults Parse(string source)
{
    var stopwatch = new Stopwatch();
    stopwatch.Start();

_input = new Input(source);
    _results = new List<IResult<InfectionFilter>>();

// First section must always parse as people filter
    var filterMatched = ParseFilter(Grammar.PeopleSection);

// Iterate through each grammar section to see if can be parsed
    while (filterMatched)
    {
        if (ParseFilter(Grammar.PersonSectionAge)) continue;
        if (ParseFilter(Grammar.PersonSectionDeceased)) continue;
        if (ParseFilter(Grammar.PersonSectionDrugBugMismatch)) continue;
        if (ParseFilter(Grammar.PersonSectionInIsolation)) continue;
        if (ParseFilter(Grammar.PersonSectionSex)) continue;
        if (ParseFilter(Grammar.AdmissionSection)) continue;
        if (ParseFilter(Grammar.AntiInfectiveSection)) continue;
        if (ParseFilter(Grammar.IsolateSection)) continue;
        if (ParseFilter(Grammar.DrugSection)) continue;
        if (ParseFilter(Grammar.ClinicalRiskSection)) continue;
        if (ParseFilter(Grammar.LaboratoryResultSection)) continue;
        if (ParseFilter(Grammar.LocationSection)) continue;
        if (ParseFilter(Grammar.SurgerySection)) continue;
        if (ParseFilter(Grammar.ObservationSection)) continue;
        if (ParseFilter(Grammar.TimeSpanSection)) continue;
        if (ParseFilter(Grammar.TimeSpanFromNowSection))continue;
        if (_input.AtEnd) break;
        filterMatched = false;
    }
}
```

DOMAIN SPECIFIC LANGUAGE TO QUERY MEDICAL DATA

FIELD

The improvements generally relate to the field of databases and information retrieval systems, and, in particular, to query languages for databases and information retrieval systems.

INTRODUCTION

A query language is a computer language to query for retrieval, manipulation and modification of information from databases and information systems. A query language is a computer language used for selecting, inserting, deleting and updating data in a database. An example query language is Structured Query Language (SQL) to retrieve and manipulate data in a relational database.

A domain-specific language (DSL) is a computer language specific to a particular application domain. A programmer using SQL to retrieve data in a database is required to construct expressions that are complicated and syntactically restricted to the variable space and table definitions in the underlying database. The programmer would typically create these expressions anew as well as validate the expressions for each new request of data from the database, resulting in an overall loss of efficiency, scalability, and reproducibility.

SUMMARY

A query device for conducting automated user identification using a domain specific query language is described. The domain specific language is a computer language specially adapted for use in the healthcare domain. The domain specific language includes specific syntax suitable to the medical or healthcare industries, and is structured in the form of a string for processing. A technical deficiency arising from relying on conventional general query languages such as SQL is an inherent lack of flexibility, an increased difficulty in use, and portability between different backend systems and data storage.

There are several reasons for not attempting to use only SQL queries to request and retrieve data. One issue is complexity. Due to the flexibility in how RLQL filters can be combined, corresponding SQL queries may be large and complex. In some embodiments, this complexity can be reduced by using SQL views, SQL code generation, and generation and storage of denormalized or transformed data ahead of its retrieval to reduce time required to present the data once it is requested. Another issue is performance, as typically it is more efficient to execute a single SQL query rather than execute multiple queries and then chain the results together. As SQL is declarative and set based, attempting to convert some RLQL expressions into a single SQL query can be challenging, for example, when needing to perform a calculation on data rows and then evaluate or compare the result of that row against other rows. It can be easier to break it up into the discrete parts. In some embodiments, this can be overcome by de-normalizing data in the dataset stored in the database. In some embodiments, simpler SQL queries can be generated to reduce the computational load (e.g., server access) or improve performance and subsequent extraction of the requested data can be performed within a .NET framework on the retrieved data. This can provide simpler evaluation and increased performance.

In some embodiments, the de-normalization can be performed dynamically or at scheduled times prior to its retrieval. This can improve computational performance, for example, relating to time, transmission, bandwidth. For example, data can be denormalized and logically stored in a new database view in a data repository to improve retrieval times measured from the time an RLQL query is received. Trend data, for example, in observations where comparisons are made between different logical rows of data to see the relative value of an observation against a previous value, can benefit from denormalization.

In some embodiments, filters are instantiated for each section determined present in a given RLQL query, where each filter is implemented with filter properties mapping the filter to a specific, corresponding database view or subset of the dataset in the data repository. This architecture, including segmented arrangement of data in the data repository and specific mapping of instantiated filters to same, can provide improved computational performance in retrieving requested data, for example, by reducing the amount of data searched in the database to retrieve the requested data, by reducing the number of accesses to a data server, or by reducing the amount of data transmitted from the server during retrieval.

For example, instead of loading a large amount of data from the data repository into .NET and then filtering to extract the relevant data, improved computational performance can be obtained if only the relevant patient data is loaded into memory within the .NET framework.

The query device, in some embodiments, is a physical hardware appliance (e.g., rack server) configured for interconnection with a messaging bus located within or coupled with a hospital data center. The query device includes one or more hardware processors operating in conjunction with computer memory and computer-readable media having instructions stored thereon which when executed, cause the hardware processors to perform querying operations in accordance with an input string. As RLQL queries are executed in some embodiments through a program using the .NET runtime, the hardware supports an operating system which can execute this. The hardware appliance also supports use of an SQL Server for data storage.

The input string is a data structure representing one or more characteristics, if all present, identify a subset of users or equipment, and is in the format of the domain specific language. The input string is received at a terminal or other input device, and transmitted to the device for conducting automated user identification.

The input string is adapted to identify characteristics that map to a subset of users, and the string is processed by the query device to computationally identify the subset of users who match all of the characteristics indicated in the provided string. In some embodiments, the input string is utilized to identify matching subsets of equipment. In an example use case, the identifiers can be used to automatically assign alerts for all users matching the requirements of the input string (e.g., place an alert on "Patients with isolate "MRSA" from test "B81.2" resistant to "AMOX"").

In the healthcare space, for example, the conducting of querying is a non-trivial computational activity. User datasets (e.g., patients, equipment, practitioners) are often high dimensional and store multitudes of data received from numerous data sources. The data may be indicative of profile information, such as date of birth, name, gender, etc. Other datasets may be obtained from secondary sources, such as equipment outputs, tracked historical chart information, pharmaceutical records, room reservation records, etc., and may be received on a synchronous, asynchronous, periodic, or continuous basis. The data may include time-stamped event data, for example (e.g., blood pressure breached a warning threshold, anaesthetic was administered, surgery was conducted on the intestines). Further, the data may also include pattern recognition-based data, estimations, probabilistic determinations, among others (e.g., user is exhibiting various symptoms of lymphoma, and an estimation of 85% confidence has been associated with the user). Other datasets may be obtained through an integration engine which integrates into different hospital interfaces, such as patient ADT movements (Admissions, Discharges & Transfers), laboratory results and medication orders. As these can be external systems from different vendors, data is not consistent, so it can be difficult to create an approach which is consistent and can adapt to different levels of data quality and content. Some embodiments of the system described herein provide consistency, for example, in data retrieval, data access, processing, and filtering, as applicable, despite various levels of data quality and content.

Data may also be provided in accordance with international standards for clinical and administrative data (e.g., HL7), and may include, for example, electronic health record/personal health record information, admission/discharge/transfer messages, physical locations, allergy information, laboratory records, insurance/billing information, among others.

The domain-specific query is automatically processed and delineated into one or more processing sections. As each user is associated with a large amount of datasets, efficient and effective querying of one or more backend data storage (e.g., databases on various servers) is an important consideration. The domain-specific query of some embodiments is specifically structured for improved efficiency through iterative processing of the one or more processing sections, where each of the one or more processing sections is classified and mapped to a specific filter (e.g., equipment, laboratory result, admission, infection).

Each filter represents a programmatic mechanism for automatically conducting a query against one or more backend data storages or other datasets to return a list of users or equipment that meet the criteria of the filter. A parser engine is provided, in some embodiments, to iteratively process, character by character, the input string to identify delineations between processing sections, to instantiate filters based on filter parameters identified within the processing sections, and to initiate processing of backend datasets (or other datasets) by the instantiated filters to programmatically reduce the search space of the query until only the users or equipment that meet all of the criteria of the input string remain.

In some embodiments, the parser engine is configured to determine the end of a section by determining when one of the following conditions are met:
1. An invalid token is entered, e.g., a character or text which doesn't match the current section being parsed is entered.
2. A keyword token for the next section is matched.
3. The end of the input string is encountered.

In some embodiments, to reduce the overall processing time required, the filters are applied against only the subset of users or equipment that remain following the application of the previous filter. In some embodiments, a mapping engine is utilized that accesses a reference table to translate terminology into filter parameters in accordance with terminology mappings.

For example, if a dataset includes 1,500,000 patients, 2,000 practitioners, and 5,000 units of equipment, rather than conducting filters across the entire dataset, the query device may be configured to, for each filter, successively reduce the search space of datasets by restricting the search space based on the outputs of the last filter. In this example, if a search is for all patients having a BMI below 23, admitted to the downtown facility within the past 24 hours, and have a staph infections resistant to amoxicillin, the filters may be successively cascaded such that each processing section (e.g., BMI, location, staph infection, drug resistance) only conducts queries against the identifiers remaining as a result of the filtering from the last processing section. Accordingly, rather than invoking a filter against a complex dataset for the 1,500,000 patients, each filter is conducted against a successively smaller set of patients. In some embodiments, filter order is modified to reduce required processing times. For example, a relatively computationally simple filter that reduces the number of identifiers down to a manageable number (e.g., 1,000 patients) may be set to precede a computationally complex filter.

For example, a lot of RLQL queries, clinicians are interested in recent events. Hospitals generate a lot of data relating to patients, but for some queries only recent data should be evaluated. An example of this is only filtering by current inpatients. So whilst a hospital may have hundreds of thousands, or even millions of patients, there will only be hundreds of patients currently admitted in the hospital at any given point in time. By filtering on those patients only, embodiments described herein can eliminate a large amount of data from being processed and increase performance.

The list of users, for example, may be returned in the form of a set of user or equipment identifiers. For example, a clinical risk filter may be utilized to identify all patients who have a risk of abdominal sepsis. Filters are instantiated based on parameters extracted from the corresponding processing section. Depending on the application, filters are instantiated through the provisioning of SQL queries, UNIX shell scripts, language integrated query languages (LINQ), multi-dimensional expressions (MDX) queries, among others. In some embodiments, the query device selectively instantiates the filters using specific underlying query languages (e.g., SQL) or frameworks (e.g., .NET) based on the identified classification of filter. In some embodiments, SQL queries can be manually generated. This provides flexibility in tailoring retrieval of data.

The query device, for each processing section, invokes the corresponding filters against backend data to automatically identify the users or equipment that match all of the criteria indicated in the input string. There are different mechanisms possible for invoking the filters against the backend data. In some embodiments, the filters are sequentially invoked. In other embodiments, the filters are invoked in parallel. In yet further embodiments, the order in which the filters are invoked may be determined automatically by the query device, and the filters may be applied successively only to remaining identifiers from prior filters.

In an aspect, there is provided a computer-implemented method for returning one or more unique identifiers identifying users or equipment in a medical environment whose characteristics satisfy one or more search criteria, the method comprising: receiving, at an input interface of a hardware processor, an expression string including one or more lexical constraints representative of the one or more search criteria, each of the one or more lexical constraints provided in an order in the string, where the order is defined by one or more section constraints of a first external domain-specific query language; parsing the expression string to extract one or more substrings from the expression string by grouping at least one of lexical constraints, words, numbers, or lists with no more than two lexical tokens, words, numbers or lists adjacent to only one other lexical token, word, number or list identified as belonging to another section, each substring representing a corresponding section within the expression string; for each substring, classifying the substring to determine a corresponding programmatic query filter type and extracting one or more programmatic query filter parameters by parsing the substring based on a reference filter parameter syntax; for each substring, instantiating the corresponding programmatic query filter based at least on the one or more filter parameters to generate one or more internal domain-specific language query strings representative of the programmatic query filter, and executing the one or more internal domain-specific language query strings to conduct query operations on one or more data stores housing multi-dimensional data sets associated with the users or the equipment to return a set of user or equipment unique identifiers that match the one or more filter parameters; combining the returned sets of user or equipment unique identifiers from each of the instantiated programmatic query filters to identify a subset of users or equipment that satisfy the one or more search criteria; and returning an output data structure storing the one or more unique identifiers identifying the users or the equipment in the medical environment whose characteristics satisfy the one or more search criteria.

In another aspect, instantiating the corresponding programmatic query filter further includes automatically determining one or more selected internal domain-specific languages from a plurality of available internal domain-specific languages, and the plurality of available internal domain-specific languages includes at least a declarative set-based query language and a procedural query language.

In an aspect, instantiating the corresponding programmatic query filter includes generating at least a first internal domain-specific language query string and at a second internal domain-specific language query string that are cascaded in operation relative to one another, the first internal domain-specific language query string conducted in a first internal domain-specific language, and the second internal domain-language query string conducted in a second internal domain-specific language; and the first internal domain-specific language is different than the second internal domain-specific language.

In an aspect, the first internal domain-specific language is a declarative set-based query language, and the second internal domain-specific language is a procedural query language.

In an aspect, the step of executing the one or more internal domain-specific language query strings includes: executing the first internal domain-specific language query string against the multi-dimensional data sets, loading only the multi-dimensional data sets associated with identifiers identified by the execution of the first internal domain-specific language query string into a short-term data structure; and executing the second internal domain-specific language query string against the multi-dimensional data sets loaded into the short-term data structure.

In an aspect, the method includes processing the output data structure to automatically update, for each of the one or more unique identifiers, a corresponding Boolean flag representative of an alert notification associated with the users or the equipment corresponding to the one or more unique identifiers, the corresponding Boolean flag indicating that the users or the equipment had been identified as a result of processing the expression string.

In an aspect, the method includes appending, for each identifier in the output data structure, on the one or more data stores in data records associated with the users or the equipment, one or more hash strings generated from a current state of the multi-dimensional data sets associated with the users or the equipment corresponding to the identifier in the output data structure.

In an aspect, the method includes processing the output data structure to automatically update the corresponding Boolean flag representative of an alert notification occurs only upon a determination that the generated hash string corresponding to the identifier is different than a prior hash string stored in the one or more data stores associated with the user or the equipment corresponding to the identifier.

In an aspect, the each substring and its corresponding instantiated programmatic query filters are executed sequentially in accordance with the order of the one or more lexical constraints; and the parsing of the expression string to extract the one or more substrings from the expression string is conducted by sequentially processing characters of the expression string from a start end to a finish end of the expression string, each programmatic query filter being instantiated and executed responsive to a parser traversing to a character representing the end of a substring.

In an aspect, there is a 1:1 mapping between the one or more substrings and the one or more internal domain-specific language query strings.

In an aspect, the method further includes: controlling a display interface to render a list of the one or more identifiers stored in the output data structure.

In an aspect, the display interface renders the multi-dimensional data sets associated with the one or more identifiers stored in the output data structure.

In an aspect, the returned sets of user or equipment unique identifiers from each of the instantiated programmatic query filters are limited to a number of unique identifiers.

In an aspect, the number of unique identifiers is dynamic and determined based on monitored load statistics of the one or more data stores.

In an aspect, each substring and its corresponding instantiated programmatic query filters are executed in parallel with respect to instantiated programmatic query filters of other substrings.

In an aspect, the instantiating of the corresponding programmatic query filter includes generating a temporary database view extracted from the multi-dimensional data sets associated with the users or the equipment corresponding to the corresponding programmatic query filter type, and the executing the one or more internal domain-specific language query strings is conducted on the temporary database view.

In an aspect, the temporary database view represents a limited subset of the data stored on multi-dimensional data sets associated with the users or the equipment corresponding to the corresponding programmatic query filter type, the limited subset of the data selected based on the corresponding programmatic query filter type.

In an aspect, responsive to the identification of a corresponding programmatic query filter type indicative of a time-duration filter type, the temporary database view representing a transformed view of data sets extracted from the multi-dimensional data sets based at least on the multi-dimensional data sets identified during the time-duration associated with the time-duration filter type.

In an aspect, the transformed view of the data sets includes at least a rolling average data record.

Corresponding systems and computer-readable media storing machine-interpretable instructions, which when executed by a processor, cause the processor to perform a method for returning one or more unique identifiers identifying users or equipment in a medical environment are provided.

In some embodiments, the system has a processor configured to: detect keystroke events as a start of a medical query expression; validate the medical query expressions; execute a search or creating a surveillance alert based on the medical query expression; parse the medical query expression into sections; create a list of filters for the sections of the medical query expression; generate an SQL query using the filters and sections of the medical query expression; execute the SQL query against a database to retrieve a list of matching patient identifiers; generate visual elements for a user interface corresponding the list of matching patient identifiers and a results summary; and trigger the display of the visual elements on the user interface.

DESCRIPTION OF THE FIGURES

Embodiments will now be described, by way of example only, with reference to the attached figures, wherein in the figures:

FIG. 8 is a screenshot of an interface for a healthcare system, according to some embodiments.

FIG. 15 depicts example pseudocode implementing an anti-infective section in a parser, according to some embodiments.

FIG. 16 depicts example pseudocode included in a parser implementing a lexicon, according to some embodiments.

FIG. 17 depicts example pseudocode included in a parser implementing a lexicon, according to some embodiments.

FIG. 18 depicts example pseudocode included in a parser implementing a lexicon, according to some embodiments.

FIG. 19 depicts example pseudocode included in a parser implementing grammar, according to some embodiments.

FIG. 20 depicts example pseudocode included in a parser implementing an architecture that parses an RLQL query, according to some embodiments.

FIG. 21 depicts an example view of a logical database table in a data repository and a corresponding SQL query, according to some embodiments.

FIG. 22 depicts an example view of SQL code in an activity view for daily medication orders, according to some embodiments.

DETAILED DESCRIPTION

Figure 1:
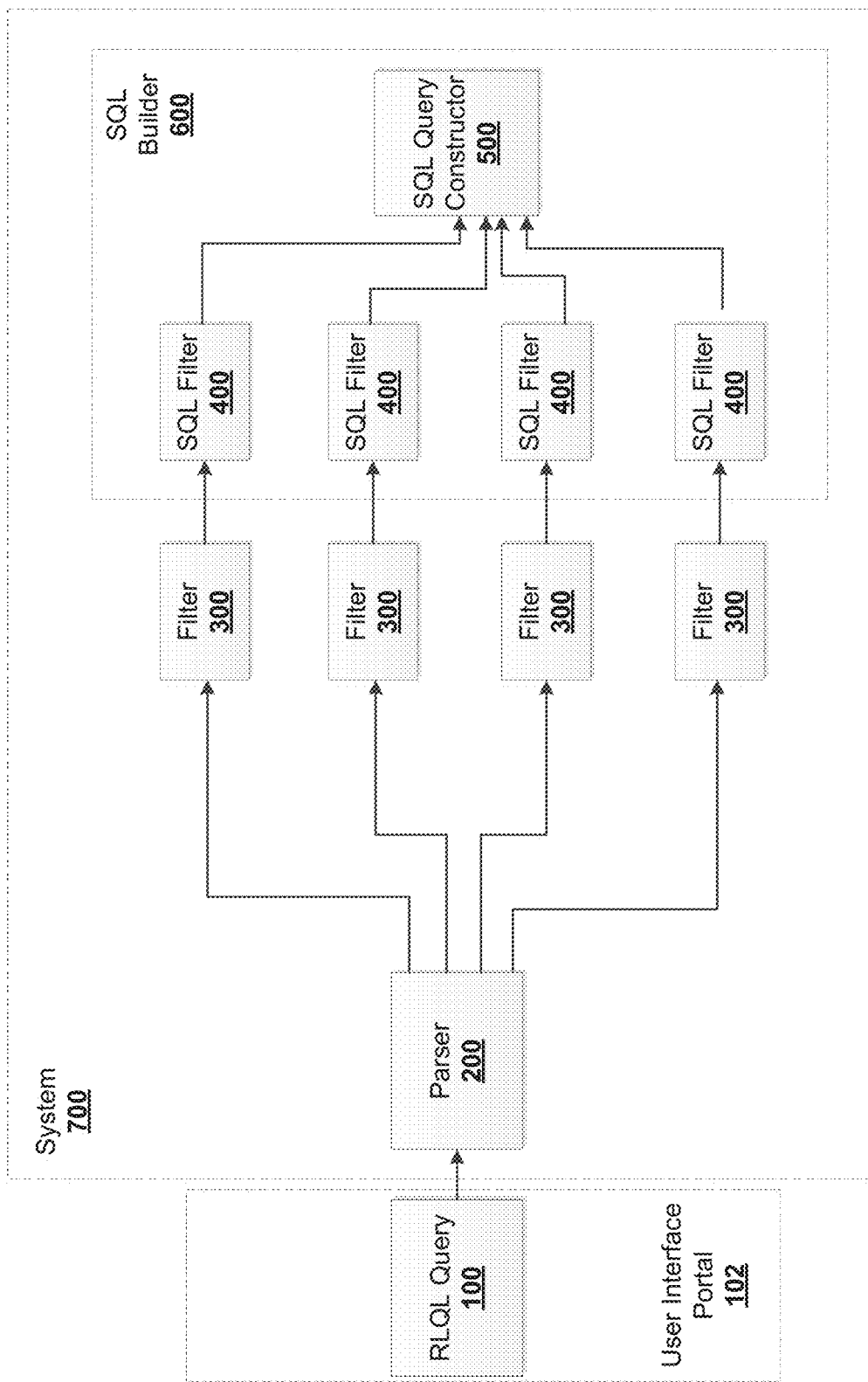
FIG. 1 is a schematic diagram of a healthcare system, according to some embodiments.

Embodiments of methods, systems, and apparatus are described through reference to the drawings.

A query device for conducting automated user identification using a domain specific query language is described. The domain specific language is a computer language specially adapted for use in the healthcare domain. The domain specific language includes specific syntax suitable to the medical or healthcare industries, and is structured in the form of a string for processing. A technical deficiency arising from relying on conventional general query languages such as SQL is an inherent lack of flexibility, an increased difficulty in use, and portability between different backend systems and data storage.

The query device is a physical hardware device that includes technical improvements to streamline processing, in view of complex, high-dimensional data sets that are prevalent in healthcare systems. Generally, there are two broad categories of domain specific languages, external and internal. An internal domain specific language uses the same language it is are written in (e.g. C#) whereas an external domain specific language is parsed independently (e.g., the external domain specific language is its own language).

The query device is a specific computer-implemented tool that is utilized to automatically conduct query operations against the complex, high-dimensional data sets to obtain a set of identifiers representative of users (e.g., patients, practitioners, visitors) or equipment (e.g., life support machines, surgical tools, rooms) that, in accordance with the high-dimensional data sets that have data records associated with the users or equipment, match the criteria indicated in a query. The implementation of such a query is non-trivial as data processing improvements are necessary to ensure that processing and identification of such users and equipment is able to be completed given finite computer processing and network bandwidth resources.

The query device is configured to perform a computer-implemented method for receiving a query in the form of an external domain specific language (e.g., one that is syntactically architected for use by administrators, and referred to as RLQL in this application) in the form of an expression string. The expression string is then parsed into sections and processed to instantiate one or more corresponding filters, the corresponding filters associated with classified filter types (e.g., infection filter, person filter, equipment filter). Pseudocode for example filters are provided in the application, alongside pseudocode for the operation of the parsers and other computing components of the query device. These filters are converted into internal domain specific languages (e.g., one that is architected for processing and conducting queries on the backend data), and executed against one or more data sets to extract identifiers that match all of the parameters of the filters.

Accordingly, the expression string is broken into a series of individual sections, which are then converted into specific programmatic query language queries that are executed against the backend data (or limited, transformed or extracted views thereof). The sets of identifiers are combined together to obtain a single output set of identifiers representative of users or equipment that met all of the requirements as indicated in the expression string. In some embodiments, to obtain performance improvements, the filters may be conducted out of order to reduce an overall search space for computationally difficult queries, or filters may utilize a combination of procedural and declarative queries.

The output set is stored in a data structure (e.g., a stored vector) of identifiers. In some embodiments, the output set is utilized to determine which users or equipment should be associated with alerts/warnings (e.g., by way of associated Boolean flags), and changes in state may be tracked, for example, by way of maintaining hashes of the underlying multi-dimensional data sets used for analysis, and only changing an alert/warning status when a presently generated hash value does not match the last maintained hash value (e.g., indicative of a change in data). The output set may be utilized to control a display interface to render a listing of identifiers that match a particular query expression string, and in some embodiments, the display interface renders additional elements indicative of other multi-dimensional data associated with the identifiers.

FIG. 1 is a diagram of an example system 700 that receives data relating to an RLQL query 100 at a user interface portal 102, for example. The user interface portal 102 is a computer application executing on a computing device to retrieve and manipulate medical data stored or accessible by system 700. System 700 may be affiliated with a healthcare facility or organization.

A RLQL query 100 is an expression string provided in the form of an external domain specific language. For example, the RLQL query 100 is a character string, and includes different components or sections. A section is a logical division of an RLQL query 100 and is defined by a grouping of one or more lexical token(s), word(s), number(s), and/or list(s). The RLQL query 100 can be received at an input interface of a hardware processor (e.g., a display touchscreen, a keyboard, a voice input).

The RLQL query 100 is used to query medical databases and information retrieval systems to filter medical data based on the statement or expression. The RLQL query 100 is used to extract, retrieve and manipulate data from medical databases and information retrieval systems. The extracted data is transformed into a readable format according to the user's specification and request. The user interface portal 102 can automatically generate RLQL queries 100 based on input data and events. For example, the user interface portal 102 can automatically detect keyboard events that correspond to expressions, concepts, and components that are used to derive the RLQL query 100.

In some example embodiments, system 700 uses the RLQL query 100 to search for patients of a health care facility and generate customized alerts for incidents in relation to the health care facility. Examples for the RLQL query 100 include: any patient with clinical risk 'EBOLA'; any inpatient on drug 'VANC' and younger than 10 years; any current inpatient in unit 'ICU' or 'NICU' for more than 48 hours; and any inpatient with isolate 'MRSA' on drug 'GENT' less than 2 days after surgery. The DSL used to generate the RLQL query 100 may be part of the Domain-Language namespace, for example. System 700 is operable to transform DSL code to generate Structured Query Language (SQL) code.

In some embodiments, system 700 is operable to transform DSL code to generate other query language code. System 700 and the RLQL query 100 enables querying of medical data in medical databases and information retrieval systems, such as medications, lab results, observations, locations, clinical risks, surgery, and the like. The RLQL query 100 can be a query of a particular data repository (e.g. databases and information retrieval systems). The RLQL query 100 can include defined timespans or time periods, relations or trends. For example, the RLQL query 100 may include a current timespan (e.g. in the last 48 hours), a time duration (e.g. for more than 8 hours), a relative time period (e.g. less than one week after), a trend (e.g. with stable or increasing condition), and the like.

The RLQL query 100 can include complex events. Further examples of RLQL queries include staff with X; patients with file X; patients with Ventilator Associated Event (VAE), Central Line Associated Blood Stream Infection (CLABSI), Surgical Site Infection (SSI); any patients with <meta>; and so on. Each section of the query is a lexical constraint that represents search criteria, as noted above in example.

System 700 uses RLQL queries 100 for different functions. System 700 uses RLQL queries 100 for querying all patients in a database for one or more hospitals using the infection surveillance application. System 700 uses RLQL queries 100 for querying an individual patient in the infection surveillance application. System 700 uses RLQL queries 100 for surveillance alerts. System 700 uses RLQL queries 100 for surveillance reporting and displaying patient records. These are illustrative examples.

Different queries 100 require different types of underlying data transformations, for example, queries relating to infection response over a time duration may require the generation of temporary database views extracted across a time-duration to show, for example, a rolling average of body temperatures for particular patients. Some sections of the queries 100 therefore may have different levels of computational resource requirements, and technical improvements are necessary, in some situations, to reduce the overall search space such that the queries can be effectively conducted. Approaches described herein to reduce the overall search space include cascading queries, running queries out of order and rather than across an entire data set, across only a selected view of the data set of relevant columns/rows/records, or across only identifiers output from prior filters.

Filter types may be ranked by overall average processing time, and in some embodiments, the order of operation of the filters may be modified such that the lowest overall average processing time operation is conducted first on the full data set, and each subsequent filter operates on the identifiers output from prior filters and are re-ordered such that the filter with the next lowest overall average processing time is conducted next, and so on until the highest overall average processing time operation is conducted on as small of a search space as possible.

In some example embodiments, system 700 uses the RLQL query 100 for ad hoc searching of patients data stored a data repository. For example, a user can interface with user interface portal 102 and select user interface elements, such as drop-down lists, radio buttons, and/or text input elements. A user interface element facilitates construction of an RLQL query. In some embodiments, system 700 is configured to populate user interface elements with values, text, tokens, lexical constraints, or section constraints that facilitate construction of one or more RLQL queries. In some embodiments, system 700 is configured to dynamically populate user interface elements based on input received from the user, for example, as an auto-complete functionality that provides best matches to acceptable input based on initial input provided by the user. System 700 receives input from the user, for example, as values selected by the user through user interface elements, and generates an RLQL query 100 based on the combination of values received or RLQL query indicated by the input received.

In some example embodiments, a user interfacing with user interface portal 102 is prompted by user interface portal 102, for example, through a visual display or message, to provide one or more RLQL queries 100. The user can provide an RLQL query 100 as free-form text, and a system 700 can receive the RLQL query 100 as one or more strings of text or as data that can be used to generate an RLQL query 100.

In some example embodiments, a user interfacing with system 700 at user interface portal 102 can view data representations corresponding to one or more specific patients, whose data is stored in a data repository accessible by system 700, and can request one or more subsets of the data relating to the one or more specific patients.

For example, the user can provide input at user interface portal 102, for example, an RLQL query 100 or selections of user interface elements that can be used to construct one or more RLQL queries 100 relating to the one or more specific patients viewed by the user. The system 700 receives the input and generates an RLQL query 100 based on the input. In some embodiments, instead of generating a RLQL query 100, the data for the specific patients is cached and system 700 filters the cached data based on the input provided by the user that encodes a request for specific data. For example, system 700 can filter the cached data within a .NET framework, rather than generating a query and accessing a data repository.

In some example embodiments, system 700 provides alerting or an alarm mechanism for actuating a response based on existing data or dynamically based on new data stored in a data repository or otherwise accessed by system 700. For example, system 700 retrieves data from the data repository corresponding to one or more RLQL queries 100 previously generated by system 700 or provided by a user to system 700. In this way, system 700 is configured to allow a hospital personnel to pre-identify important events, for example, incidence of drug bug mismatches (inappropriate prescription of antibiotics), abnormal observations or laboratory results, or re-admission of patients with history or symptoms of infection following surgical procedures, and set up a workflow for more accurate and timely recognition of and response to the important events.

System 700 includes a parser 200, one or more filters 300 that may each be associated with one or more SQL (or other language) filters 400, and an SQL (or other language, as appropriate) query constructor 500. Query builder 600, query constructor 500, and filters 400 can generate code in one or more other query languages. In the embodiments described herein, SQL is used as one such example query language.

The DSL code used to generate RLQL query 100 includes lexicons, grammars, and parsers 200. The lexicon is used to define value vocabulary (e.g. words, numbers, attributes, lists). The lexicon maps items of the vocabulary to enumerations. The grammar defines valid constructs from the lexicon to generate the RLQL query 100. The grammar is divided into sections to facilitate parsing and filtering. The sections instantiate filters 300. A lexical constraint can be referred to as a lexicon, lexical token, and/or token and includes words, numbers, and lists. A sectional constraint can be referred to as a section, grammar section, grammar, and/or grammar constraint. In some embodiments, lexical constraints and sectional constraints are implemented by a parser 200 and used to identify sections present in an RLQL query 100 and instantiate corresponding filters 300. In some embodiments, a parser 200 processes an RLQL query 100 into valid grammar sections, each grammar section to be parsed into a filter 300.

For each filter 300, the parser 200 may then create an SQL filter 400 or use an SQL filter 400 already associated with the filter 300 to construct one or more SQL queries that correspond to the RLQL queries 100. An SQL filter 400 translates filter 300 properties into SQL queries. For example, for a particular filter 300, SQL builder 600 is configured to generate a corresponding SQL (or other language) filter 400 that includes a property identifying a specific parameter in a data repository that can be used by system 700 to retrieve data corresponding to the filter 300 or RLQL query 100 or dataset (or subdataset) indicated by RLQL query 100. As an example, for a filter 300 instantiated based on a "drug" section in an RLQL query 100, in some embodiments, SQL builder 600 is configured to generate a corresponding SQL filter 400 that includes a property identifying a specific logical data table and/or a specific logical data table column where different values for "drug" are stored. SQL builder 600 constructs an SQL query based on all the one or more different SQL filters 400 corresponding to the RLQL query 100, including the respective properties included in each filter 400 that identifies the respective specific logical tables and/or specific logical data table columns.

Conducting the queries may include generating a temporary database view extracted from data sets associated with the users or the equipment corresponding to the corresponding programmatic query filter type. For example, a drug-type filter may require a specific database view that is prepared in response to a classification that a drug-type filter will be instantiated. The temporary database view represents a limited subset of the data and is adapted for improved processing time by restricting the amount of information to be processed. Where time-duration filters are utilized, or other types of filters needing transformation of raw data, the temporary database view may be generated based on a transformed view of data sets extracted from the multi-dimensional data sets based at least on the multi-dimensional data sets identified during the time-duration associated with the time-duration filter type. For example, time-ended drug data over the past 24 hours may need to be processed and transformed to obtain various types of data for the patient, such as rolling average of medication administered or present in the blood stream, etc.

SQL builder 600 constructs SQL queries using an SQL grammar. The SQL grammar is defined in relation to a data structure logically representing data stored in a data repository, for example, table and columns identifiers as well as directional and numerical relationships between tables. System 700 uses an RLQL query language for RLQL queries 100. System 700 is configured to construct filters based on sections present in an RLQL query 100 received by system 700, for example, at user interface portal 102 or from an external system or server. System 700 instantiates filters 300 for each section present in the RLQL query 100, where each filter 300 is instantiated with one or more properties corresponding to the section type and/or values in the RLQL query 100 within the corresponding section. System 700 maps filter properties to the data structure in the data repository storing the relevant dataset, for example, to a database storing hospital patient data. The SQL grammar or query may comprise lexical tokens, words, numbers, and/or lists that are defined by an SQL lexicon and are organized or ordered in a way defined as valid by one or more SQL grammar constraints. Individual lexical tokens may include lexical tokens, words, numbers, and/or lists, and may include other tokens.

In some embodiments, SQL builder 600 comprises one or more SQL filters 400 and an SQL query constructor 500. Each SQL filter 400 is associated with a filter 300 in some embodiments. One or more filters 300 and/or SQL filters 400 may be used by SQL builder 600 via SQL query constructor 500 to generate a query for the medical database or information retrieval system. That is, an SQL query constructor 500 may receive data from one or more filters 300, SQL filters 400 and create an SQL query that may be used to query one or more databases and return the queried data. Filters 300 find data that matches the DSL definition. In some embodiments, each result filter 300 maps to a corresponding SQL filter 400.

SQL builder 600 may be used to build one or more complex or simple SQL statements based on parameters specified by the RLQL query 100 such as file types, a user's scope, and a user's view cache. SQL builder 600 may assist with speed of the functionality of system 700 and/or the ease with which it may be modified. Implementation of the connection to one or more databases may use Linq2SQL or OrmLite, for example. SQL builder 600 provides a consolidated view used to construct SQL queries from the RLQL query 100.

In this way, one or more filters 300 and/or SQL filters 400 may be used to find data that matches or corresponds to an RLQL query 100 or definition. This may increase the ease and/or efficiency with which data in one or more databases is found. For example, an RLQL query 100 may be used as input to easily query complex events, for example, Ventilator Associated Event or Central Line-associated Blood Stream Infection. The SQL builder 600 may enable ad-hoc querying using RLQL queries 100 and/or functionality enabling a search of data in one or more databases.

In some embodiments, one or more filters 300 may be used without any SQL filters 400 to generate a query on the database. In some embodiments, SQL builder 600 may include a consolidated database view that is used to construct an SQL query from received RLQL queries 100. System 700 also includes search and alert features. For example, search may be used for ad-hoc querying and constructing RLQL queries 100 via the SQL builder 200. Alerts can be implemented using filters 400 to generate has code of criteria for alert triggers and to avoid alert re-triggers if needed.

In some embodiments, system 700 can filter data within a .NET framework, once the data is received from a data repository.

For example, system 700 generates or instantiates one or more filters 300 based on an RLQL query 100 received at user interface portal 102. The filters 300 can be instantiated based on a process described above. For example, a parser 200 determines sections present in the RLQL query 100 based on lexical constraints and section constraints, including enumerations. The parser 200 instantiates a filter 300 for each section determined present in the RLQL query 100. System 700 uses each filter 300 (e.g., filter properties containing relevant values from the RLQL query 100) to generate a filter 400 that can be used to generate one or more SQL queries (or other language implementing data retrieval techniques from data repositories).

In some embodiments, SQL filters 400 are generated by system 700 in the following way. SQL queries rely on .NET to build the SQL text for an associated filter. For example, the RLQL query, "any current inpatients on drug 'Penicillin' in the last 3 days", is parsed by parser 200 into three different filters, the first a people filter, the second a drug filter, and the third a timespan filter. This list of filters is then passed by parser 200 to an SQL builder class 600, where system 700 is configured to use the people filter to construct the first part of the SQL query, i.e., only include current inpatients. The drug filter would then further filter on data that can be retrieved by system 700 using the previous filter, i.e., current inpatients administered Penicillin. System 700 is then configured to use the final filter to further filter data retrieved by the previous filter, i.e., patients administered Penicillin in the last 3 days. In this way, system 700 is configured in some embodiments to improve database querying by overcoming complexity associated with large SQL queries, while providing a flexible query language. This can improve computer performance, for example, as it can be more efficient to execute a single SQL query rather than execute multiple queries and then chain the results together.

System 700 is configured in some embodiments to filter data retrieved by the one or more SQL (or other language) queries within a .NET framework. Example embodiments where system 700 is configured this way follow.

In some embodiments, one or more SQL queries are generated that when executed against a data repository will together retrieve a dataset larger than requested or indicated by the RLQL query 100. For example, in some embodiments, an SQL query generated may retrieve the patients indicated by the RLQL query 100 as well as patients without one of the constraints indicated by a section in the RLQL query 100.

In some embodiments, every RLQL filter 300 has a corresponding SQL filter class 400 that system 700 uses to construct SQL queries to access data corresponding to a RLQL query 100. In some embodiments, system 700 provides functionality to generate one or more SQL queries that can be executed over a dataset to retrieve only a dataset exactly corresponding to data indicated by an RLQL query 100. For example, generating such SQL query or queries (e.g., where one-to-one mapping between a dataset requested by an RLQL query 100 and a dataset retrieved by an SQL query generated) may be technically challenging where different timespan filters must be chained together, that is, where one or more timespan filters 300 is used by system 700 to filter on results that will be retrieved by another timespan filter 300. An example of this technical situation is encountered when system 700 receives the following RLQL query 100: "any current inpatients on drug 'Penicillin' for more than 2 weeks in the last 3 months". Processing this RLQL query 100 requires a very different SQL query than "any current inpatients on drug 'Penicillin' in the last 3 months". The latter is far easier to evaluate, as it only has to compare against a single date/time value in one table row, whereas the former needs to compare its own date/time against other rows. In some embodiments, system 700 ensures the data presented to a user exactly corresponds to the data indicated by an RLQL query 100 that the user provides. For example, in such embodiments, system 700 generates a simpler SQL query and executes the query to retrieve a larger dataset than that indicated by the RLQL query 100. System 700 then applies additional filtering using filters 300 on the dataset to extract indicated by the RLQL query 100. In this way, system 700 reduces the computational load associated with execution of large SQL queries including complex operations (e.g., complex joins on logical tables) and/or the computational load associated with required server or database accesses associated with large, complex SQL queries.

In some embodiments, there may be an RLQL query 100 that no SQL query can exactly correspond to or be generated to retrieve the same dataset. One example is inverted Boolean logic, as it is not currently supported for SQL code generation. In these cases, for example, it is more difficult to exclude non-matching data than it is to include matching data. An example RLQL query 100 is "any current inpatients not on drug 'Penicillin' for more than 2 weeks in the last 3 months". This inverted "not on drug" query is more difficult to construct in SQL than an "on drug" query. Embodiments of system 700 improve data retrieval by generating a simpler SQL query and subsequently performing additional filtering within a .NET framework (where computational operations can require less computational resources, for example) to generate a dataset exactly corresponding to that requested by an RLQL query 100.

In some embodiments, it may be preferred to reduce the load on a server housing or providing access to the data repository or to improve performance times or the efficiency with which the computer retrieves data from the data repository. To address this, system 700 is configured to generate a reduced number and/or reduced complexity of SQL (or other language) queries from the RLQL query 100 (according to a process described herein). This can improve performance, for example, reduce accesses to a server or database that would otherwise be more timely or costly than computer operations run locally. In this way, system 700 is configured to generate one or more SQL (or other language) queries that when executed against a data repository will together retrieve a dataset larger than requested or indicated by the RLQL query 100.

To address these example embodiments or to improve the correspondence between a RLQL query 100 and the data retrieved by the computer from a data repository, in some embodiments, system 700 is configured to apply additional filtering techniques within a .NET framework, where the additional filtering techniques are applied on the dataset retrieved by the one or more SQL queries. The filtering techniques within the .NET framework filter or extract a subset of the dataset retrieved from the database, where the subset corresponds to the RLQL query 100 or instantiated filters 300. For example, a filter corresponding to each section determined in the RLQL query 100 can be executed over the dataset and the results of each execution can be combined to form a new dataset comprising only the data indicated relevant by the RLQL query 100.

An example of this is location scope. Given a database which contains data from multiple hospitals, a user may be authorized via their role to view all data from "Hospital 1" only, while a patient may have data in both "Hospital 1" and "Hospital 2". When the user provides an RLQL query 100 to system 700, all data from "Hospital 2" should be excluded before any further processing takes place as that location is out of their scope. In some embodiments, system 700 is configured to restrict the user's access based on security permissions before any data is retrieved from a database, thereby improving execution times and database accesses when the user requests data by providing an RLQL query 100. Further, in some embodiments, the dataset is logically arranged to provide certain database views containing discrete subsets of data. A given user has an account used to authenticate the user with system 700 before access is provided to system 700. The account data can include a parameter or parameters specifying one or more database views that the user is permitted to access and/or not permitted to access. System 700 can generate a SQL query corresponding to the user's provided RLQL query 100 that excludes access to logical tables (or other data storage structure or data field), based on the one or more parameters stored with the user's login account representing the user's security permissions.

This can allow, for example, a simpler SQL query to be generated from filters 300 instantiated from an RLQL query 100, where the SQL query is constructed to improve computer performance by involving fewer operations and retrieving, when executed, a larger dataset than indicated by the RLQL query 100. System 700 is configured to then retrieve the exact dataset matching the RLQL query 100 by filtering the larger dataset returned by the SQL query, for example, based on the filters 300 previously instantiated from the parsed RLQL query 100. This additional layer of filtering can be performed within a .NET framework, for example, and can reduce the load on servers housing the database or data repository, where the load is due to the complexity or number of queries executed or due to the number or nature of the accesses to a server, database, data repository, logical data tables, or other logical storage structure.

In some embodiments, the SQL queries generated from RLQL filters only return a distinct list of patient identifiers. The complexity of SQL code generation can lie, for example, in the joining of relational data and the associated predicates for each join.

In some embodiments, for each patient from the result of an SQL query matched by an RLQL query 100, system 700 performs an in-memory load of the associated patient data for evaluation in .NET.

In some embodiments, system 700 is configured to retrieve only the minimal amount of information required to identify all data entries in a desired dataset. For example, system 700 is configured to retrieve only the patient identifiers for the patients requested in an RLQL query 100. This can reduce the load on a database, other storage structure, or one or more servers housing the database or other storage structure. This can also reduce transmission costs (or improve transmission performance, for example, by reducing bandwidth required or latency) of retrieving the requested data from the data repository housing the data and of storing the data within system 700. In some embodiments, system 700 is configured to then retrieve relevant data from the data repository using the patient identifiers in portions or at different times when needed.

In some embodiments, system 700 is alternatively or also configured to retrieve the relevant data from cached data using the patient identifiers. In some embodiments, the patient identifiers retrieved from the data repository may include identifiers in addition to those corresponding to data requested by an RLQL query 100—for example, an SQL query can retrieve patient identifiers corresponding to a larger dataset than requested by an RLQL query 100. In these embodiments, system 700 is configured to filter the retrieved identifiers to extract only those relevant identifiers.

In some embodiments, system 700 is configured instead to request from local caches or storage or retrieve from a data repository (e.g., using one or more SQL queries) other data fields referenced by the retrieved identifiers (e.g., patient data corresponding to each patient identified by the retrieved identifiers) and then filter the retrieved data to extract only those data indicated relevant by the RLQL query 100.

System 700 is configured to perform such filtering using the filters 300 that were instantiated based on the sections identified by parser 300 in the RLQL query 100 (or filters 300 newly instantiated using the same or some of the same parameters or based on the same sections).

In these ways, the SQL builder 600 can generate an SQL query that, when executed over a dataset in a data repository, returns a larger dataset than the one indicating by the RLQL query 100. Subsequent filtering can be performed on the larger dataset to extract only the data corresponding to data indicated by the RLQL query 100. This architectural separation allowing multi-tiered data retrieval and filtering can ensure all data corresponding to an RLQL query is presented to a user at user interface portal 102 or transmitted to an external system, for example, where there is no one-to-one mapping between filters 300 and SQL filters 400 or between an RLQL query and SQL query or where it is desirable to improve computational performance or reduce the load on database or server access. A discrepancy may lie in the differences between the two systems, i.e., SQL is a declarative set based system, whereas the RLQL code uses .NET which is (mostly) a procedural system, so there can be an inherent mismatch.

Some embodiments overcome this discrepancy as described herein. A combination of the procedural and declarative set based query languages can be utilized to obtain a technical processing benefit, for example, by conducting a first declarative query (e.g., SQL query) to reduce a search space, and then a procedural query (e.g., .NET query) on the outputs of the first declarative query rather than across the entire available data set. The declarative query is efficient for conducting simple, low processing cost operations (e.g., checking records to compare against a simple condition) across the data set to reduce the search space, while the procedural query is more efficient for conducting higher processing cost operations (e.g., requiring the computation or transformation of values generated from underlying data records). The cascaded query provides technical improvements to improve processing times or reduce overall resource requirements.

Figure 2:
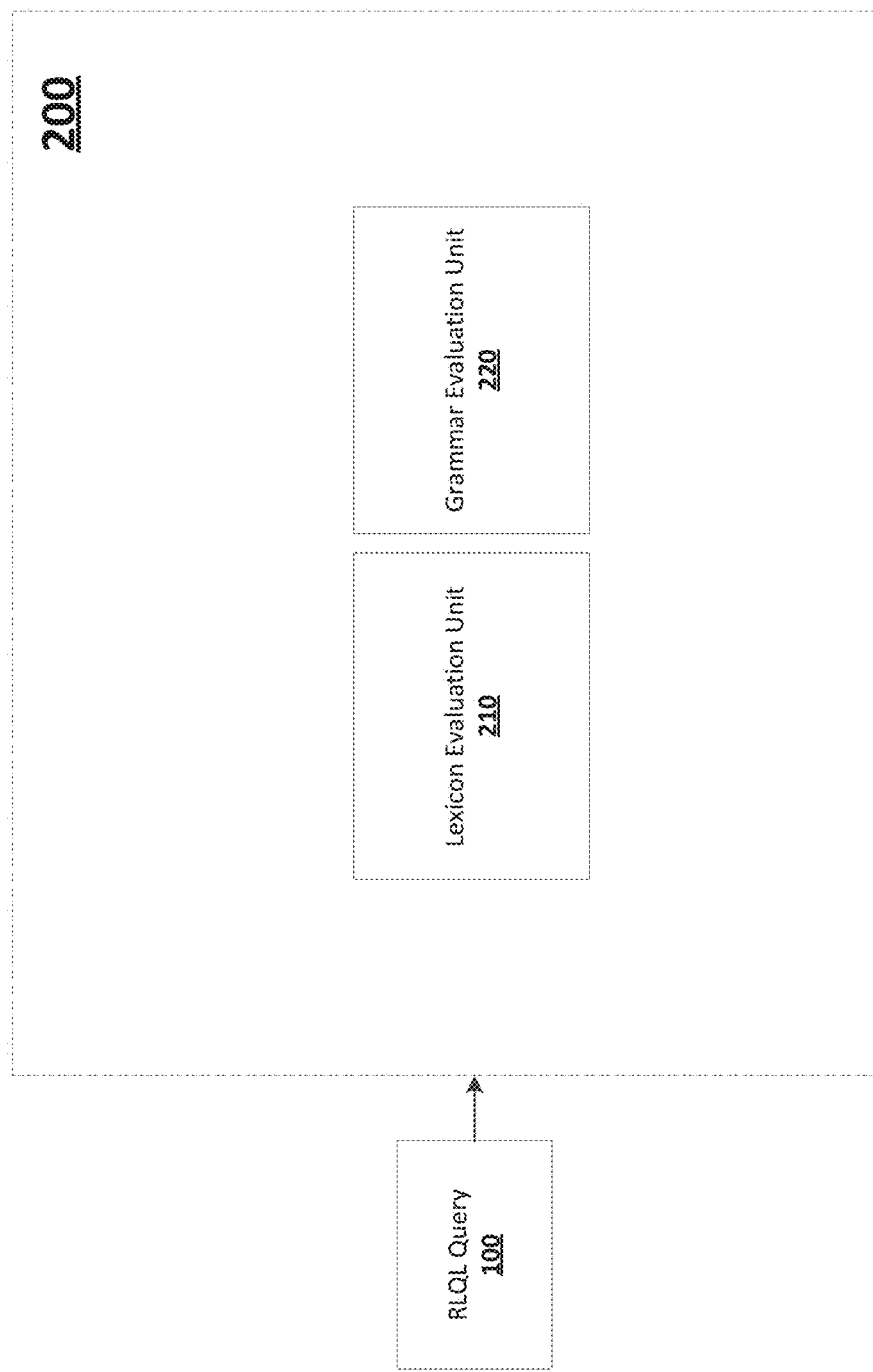
FIG. 2 is a schematic diagram of a parser of a healthcare system, according to some embodiments.

FIG. 2 is a diagram of an example SQL builder 200 that receives data relating to an RLQL query 100. SQL Builder 200 receives filter 300 properties. In some embodiments, filter 300 properties are used to generate SQL queries based on the RLQL queries. SQL Builder 200 may use a lexicon evaluation unit 210 and a grammar evaluation unit 220 to generate the SQL queries and map the SQL lexicon and grammar to the RLQL lexicon and grammar. For example, in some embodiments, an SQL filter 400 is instantiated for each filter 300 instantiated from sections identified by parser 200 in a RLQL query 100 received by system 100. SQL filter 400 is instantiated using properties of its corresponding filter 300, for example, for the Admission filter, properties specifying ", not admitted from Toronto". In some embodiments, all SQL filters 400 that are instantiated based on the same RLQL query 100 are used by SQL Query constructor 500 to construct an SQL query (or multiple simpler SQL queries, for example, to optimize computational performance, database access times, server performance, or transmission times or bandwidth usage). The SQL query or queries are constructed to retrieve only exactly the dataset defined by the RLQL query 100.

In some embodiments, as described herein, the SQL query or queries are constructed to retrieve a larger dataset than indicated by the RLQL query 100. In such embodiments, system 700 is configured to filter the retrieved dataset using filters 300 instantiated based on the sections present in the RLQL query 100, that is, to extract only exactly the dataset defined by the RLQL query 100. As described herein, this can improve the computational performance for presenting a user with the data requested from the database or data structure stored in the data repository. For example, server-side or database operations may be computationally costly, requiring intolerable time, memory, storage, or bandwidth. Using an SQL query that requires fewer server-side or database operations (e.g., joins between multiple logical tables), for example, can be preferable, even where the SQL query retrieves a larger dataset.

The SQL query generated can limit the distinct number of patients returned. For example, system 700 can be configured with a default setting to limit the return to the top 200 patients. For example, a user may provide to system 700 an RLQL query 100, "any patient on drug 'Aspirin'". As this RLQL query 100 includes all patients with no timespan, it would potentially match on a very large result set, thus consuming a lot of computational resources and slowing response time. By reducing the maximum number of results to 200, system 700 improves performance (e.g., reduces bandwidth consumed) and usability (e.g., perceived immediate generation of data to a user) for retrieving data as it helps ensure a reasonable set of data is managed (e.g., retrieved from databases at a data repository, transmitted from database server, processed at system 700, etc.) and a reasonable response result is produced.

An RLQL query 100 may be an expression or statement of components or sections. A section is a logical division of an RLQL query 100 and is defined by a grouping of one or more lexical token(s), word(s), number(s), and/or list(s) that may be, for example, adjacent to one or two other lexical tokens, words, numbers, or lists belonging to the same section with no more than two lexical tokens, words, numbers, or lists adjacent to only one other lexical token, word, number, or list belonging to the same section. That is, a section may comprise a string of lexical tokens, words, numbers, or lists that is not intervened by any words, numbers, or lists not belonging to the same section. The use of sections may increase the ease of parsing and filtering of an RLQL query 100 by parser 200. A section may instantiate a corresponding filter 300. The logical division of an RLQL query 100 into one or more sections may be followed by a filter 300 corresponding to each section being applied to the RLQL query 100. A filter 300 corresponding to each section may also be applied to an RLQL query 100 that has already had one or more filters 300 applied to it.

Grammar evaluating mechanism 220 and/or lexicon evaluating mechanism 210 may store, receive, transmit, or update constraints relating to lexicon, grammar, and/or sections. Lexicon constraints define valid vocabulary, words, numbers, and lists and map same to enumerations. Grammar constraints define valid constructs from a lexicon and may logically divide an RLQL Query 100 into sections. The use of sections may increase the ease of parsing and filtering an RLQL Query 100 by parser 200.

In some embodiments, the grammar constraints may include the following constraints of what may be parsed:

$_{opt}$ denotes a section that is optional and may be omitted;

( ) denotes a lexical token that is optional and may be omitted;

[|] denotes a set of lexical tokens, one of which must be selected, unless the set itself is surrounded by ( );

◊ denotes a selected pick list item which must be surrounded by ' (single quotes);

(or ' . . . ) denotes optional, additional pick list items, for example, 'A' or 'B' or 'C';

< > refers to a .NET type, such as <int>, <double>, or '<string>'

<int> (where int denotes a whole number, for example, 2);

<double> (where double denotes a number, for example, 2.4);

'<string>' (where string denotes free text, for example, 'Risk');

As noted, the RLQL query 100 may be an expression that includes one or more sections. The sections may be parsed by parser 200 for provision to filters 300. The sections include tokens from the syntax of the DSL code. The sections may be connected by the constructs, such as the examples shown above.

There may be people-section, which may have the following syntax:

((any) ((person who is) (not) (a|an))) [patient(s)|inpatient(s)|current inpatient(s)]

There may be an admission-section, which may have the following syntax:

(,) (and) (not) [admitted|admission|readmitted|readmission] (from '{Source}' (or ' . . . )) There may be an antiinfective-section, which may have the following syntax:

(,) (and) (is|being) (not) on [antiinfective|antibiotic] ('{Antiinfective}'(or ' . . . )) (in [class|group]'{Class}'(or' . . . )) (delivered (via) '{Method}') (at [facility|unit|building|floor|room|bed|icu|neonatal] ('{Location}' (or ' . . . )))

There may be admission-section$_{opt}$,timespan-section$_{opt}$, which may have the following syntax:

(,) (and) (not) [admitted|admission|readmitted|readmission] (from '{Source}' (or ' . . . ))

There may be anti-infective-section$_{opt}$,timespan-section$_{opt}$, which may have the following syntax:

(,) (and) (is|being) (not) on [antiinfective|antibiotic] ('{Antiinfective}' (or ' . . . )) (in [class|group] '{Class}' (or ' . . . )) (delivered (via) '{Method}')

There may be clinical risk-section$_{opt}$,timespan-section$_{opt}$, which may have the following syntax:

(,) (and) (having|with) clinical risk '{Risk}' (or ' . . . ) (and comment (contains) '<string>')

There may be drug-section$_{opt}$,timespan-section$_{opt}$, which may have the following syntax:

(,) (and) (is|being) (not) on drug '{Drug}' (or ' . . . ) (in [class|group] '{Class}' (or ' . . . )) (delivered via '{Method}')

There may be isolate-section$_{opt}$,timespan-section$_{opt}$, which may have the following syntax:

(,) (and) (not) (having|with) isolate (['{Organism}' (or ' . . . )|from test '{TestType}' (or ' . . . )]) (of interest) ([resistant|sensitive|susceptible|intermediate] to '{Antimicrobial}' (or ' . . . ))

There may be laboratoryresult-section$_{opt}$,timespan-section$_{opt}$, which may have the following syntax (,) (and) (having|with) lab result (having|with) (stable (or)) (decreasing|increasing) ('{TestResult}' (or ' . . . )) (from test '{TestType}' (or ' . . . )) (ordered by '<string>' (or ' . . . )) (with status '{Status}' (or ' . . . )) (of|by more|less than <double> ('{LaboratoryUnit}'))

There may be location-section$_{opt}$,timespan-section$_{opt}$, which may have the following syntax:

(,) (and) (is) (not) (being) in [(any) location|facility '{Facility}' (or ' . . . )|unit '{PointOfCare}' (or ' . . . )|building '{Building}' (or ' . . . )|floor '{Floor}' (or ' . . . )|room '{Room}' (or ' . . . )|bed '{Bed}' (or ' . . . )|icu|neo natal icu]

There may be observation-section$_{opt}$,timespan-section$_{opt}$, which may have the following syntax:

(,) (and) observed with (stable (or) (decreasing|increasing)) '{Observation}' ((of|by) more|less than <double> ('{ObservationUnit}'))

There may be person-section$_{opt}$,timespan-section$_{opt}$, which may have the following syntax:

(,) (and) (who) (are|is) (not) older|younger than <int> year(s)|month(s)

(,) (and) (who) (are|is) (not) deceased (,) (and) (who) (has|have|does not have) (a) drug bug mismatch (,) (and) (who) (are|is) (not) in isolation (,) (and) (who) (are|is) (not) [male|female]

There may be surgery-section$_{opt}$,timespan-section$_{opt}$, which may have the following syntax:

(,) (and) (having|with) (no) surgery (in specialty) ('{Surgery|Specialty}' (or ' . . . ))

The timespan-section may have either of the following syntax:

in (the) [last|next]<int>[minute(s)|hour(s)|day(s)|month(s)|year(s)]

(for) [at least|at most|more than|less than|equal to|within] <int> [minute(s)|hour(s)|day(s)|week(s)|month(s)|year(s)] ([before|after|during])

In some embodiments, once an expression is parsed, data is then filtered.

Lexicon evaluating mechanism 210 may evaluate an RLQL query 100 by processing each lexical token, word, number, and/or list and may evaluate whether the lexical token, word, number, and/or list match lexical tokens, words, numbers, and/or lists defined as valid according to one or more lexicon constraints. Lexicon evaluating mechanism 210 may associate a lexical token, word, number, and/or list with an enumeration and may store and/or transmit data relating to the association, for example, to enable, facilitate, and/or assist with multiplicity to multiplicity associations between filters 300 and/or 400. Lexicon evaluating mechanism 210 defines and updates the lexicon of all words or characters in the DSL code, including combinations of words.

Grammar evaluating mechanism 220 may evaluate an RLQL query 100 by processing one or more lexical tokens, words, numbers, and/or lists in concert. Grammar evaluating mechanism 220 may evaluate whether said lexical tokens, words, numbers, and/or lists processed in concert match constructs of lexical tokens, words, numbers, and/or lists defined as valid according to one or more grammar constraints.

Parser 200 may process an RLQL query 100 using a lexicon evaluating mechanism 210 and a grammar evaluating mechanism 220. Parser 200 may parse valid input from grammar sections into result filters 300.

Lexicon evaluating mechanism 210 defines and updates the lexicon of all words or characters in the DSL code, including combinations of words For example, the lexicon may define the following words or characters:

"unit" is a single word.

"more than" is commonly used combination of words.

"year", "month", "week", "day", "hour" and "minute" are single words that map to an enumeration to cover an event duration. These may be used for filtering against domain data.

Grammar evaluating mechanism 220 defines and updates the grammar for the DSL code. The grammar defines the valid combinations of words or characters from the lexicon. These are separated into sections which match specific domain requirements. Example defined domain sections include: Admission, Anti-infective, Clinical Risk, Drug, Isolate, Laboratory Result, Location, Observation, Person, People, Surgery and Timespan. An admission encompasses ADT, or Admission, Discharge and Tranfers (bed movement) events. Anti-infection refers to anti-infectives or antibiotics prescribed to patients. Anti-infectives are also filtered by their delivery method (injected, orally, etc.) and drug class (group of drugs it belongs to). Drug refers to medications prescribed to patients. These are typically captured through integration with pharmacy orders. Isolate refers to the separation (isolation) of organisms from a culture for testing purposes.

RLQL query 100 also filters by an isolate sensitivity or resistance to an antimicrobial, or the isolate test type. Location can refer to a physical place inside a medical facility. This can be broken down into a hierarchy defined as follows: facility, point of care, building, floor, room, bed. There are also custom cross-cutting locations, Intensive Care Units (ICU) and Neo-Natal Intensive Care Units (NICU). Observation can refer to clinical observations, e.g. blood pressure, patient temperature. Timespan can be used filter a section by a duration, or filter sections joined together by a duration.

For example, the grammar may define the following:
"any current inpatients" maps to the People section in the grammar.
"having surgery 'HIP'" maps to the Surgery section in the grammar.
"in the last 48 hours" maps to the TimeSpan section in the grammar.

Parser 200 validates an input expression against the grammar, mapping valid sections of the expression to create one or more filters 300. For each domain section there can be a corresponding class of filter 300.

For example, given the input expression:
"any current inpatients in unit 'ICU' or 'NICU' for more than 2 weeks"

Parser 200 validates the characters of the RLQL query 100 by determining if there are valid matches in the lexicon by invoking lexicon evaluating mechanism 210. For example,
"any current inpatients" is a valid match for the person section in the grammar.
"in unit 'ICU' or 'NICU'" is a valid match for the location section in the grammar.
'ICU' and 'NICU' are based on a list of related terminology items.
"for more than 2 weeks" is a valid match for the timespan section in the grammar.

Filters 300 are grouped into classes and contain properties and methods required for each domain section to filter medical or patient data to generate results. Filters 300 are created and populated by the parsing of grammar by parser 300. Each filter 300 also has an associated SQL builder class for creating SQL queries based on the filter's 300 properties.

Each filter 300 generates results by filtering medical data from database on data storage. For example, given a list of people (e.g. patients) as an RLQL query 100. Each filter 300 from an input expression of the RLQL query 100 is evaluated to find matches. The list of people used as input for the RLQL query 100 depends on the particular workflow being used. For example, for general patient queries and surveillance alerts, the SQL builder 600 can generate SQL queries that correspond to RLQL queries 100 from filters 300 to query a database of medical data to generate results. As another example, for individual patient queries, filtering may be done against a patient model.

FIG. 15 depicts example pseudocode implementing an anti-infective section in a parser 200. As shown for the Anti-Infective section, each section maps to its associated filter. A successfully parsed section in the grammar instantiates a filter.

In some embodiments, system 700 is configured to correctly identify sections in an RLQL query 100, irrespective of the order that the sections in the RLQL query are in. Each section uses specific keywords unique to that section. For example, the keyword phrase "on antiinfective" is unique to the anti-infective section.

Parser 200 can parse an RLQL query 100 according to a lexicon and grammar. In some embodiments, parser 200 includes a layer using a combinator parser, such as Sprache™. The layer above this defines a lexicon, which is divided into three parts. Each property in the lexicon is a generic Parser type found in Sprache™, allowing different words and tokens to be combined together.

FIG. 16 depicts example pseudocode included in a parser 200 implementing a lexicon for system 700 according to some embodiments. As shown, the lexicon defines single words and can be used to parse an RLQL query 100 by assigning the words to variables where present in the RLQL query 100. Only an example selection of the words included in a lexicon according to some embodiments are shown. Parser 200 is configured to parse an RLQL query 200 with case insensitivity, for example.

FIG. 17 depicts example pseudocode included in a parser 200 implementing a lexicon for system 700 according to some embodiments. As shown, the lexicon defines combinations of words and can be used to parse an RLQL query 100. Only an example selection of the combined words included in a lexicon according to some embodiments are shown. Parser 200 is configured to parse combinations of single words; this can be used to allow consistency in grammar usage in an RLQL query 100 received.

FIG. 18 depicts example pseudocode included in a parser 200 implementing a lexicon for system 700 according to some embodiments. As shown, the lexicon defines enumerations and can be used to parse an RLQL query 100. Only an example selection of the combined words included in a lexicon according to some embodiments are shown. Parser 200 can be configured to implement enumerations that use either single or combined words and map them to .NET enumerations defined in a domain model.

FIG. 19 depicts example pseudocode included in a parser 200 implementing a grammar logical layer that receives or uses the defined lexicon. Parser 200 is configured to implement the grammar by defining sections or arrangements of words and connectors. As shown, an RLQL query 100 containing an admission section, as detected using parser 200, can be used by parser 200 to instantiate a corresponding filter.

FIG. 20 depicts example pseudocode included in a parser 200 implementing an architecture that parses an RLQL query 100 by determining which grammar sections are present in the RLQL query 100. For each section present, parser 200 instantiates a corresponding filter based on filter properties that includes content from RLQL query 100. In this way, parser 200 takes an input string (i.e., RLQL query 100) and generates a list of filters corresponding to the grammar sections present in the input string. Parser 200 is not configured to limit the number of filters than can be generated; as long as the section being parsed is valid, the system 700 will generate the corresponding filter. On the evaluation side, a list of patients can be passed to test against each filter in the result list.

In some embodiments, each filter contains all of the information needed to evaluate if a patient matches. Each filter also contains all properties needed by system 700 to construct one or more SQL queries to filter by. In some embodiments, for example, there is a 1:1 mapping between filters 300 and SQL filters 400.

In some embodiments, system 700 generates SQL queries using a template-driven approach, where each SQL filter 400 is generated based on the corresponding filter 300 and instantiated with properties identifying the corresponding database table and columns.

Figure 21:
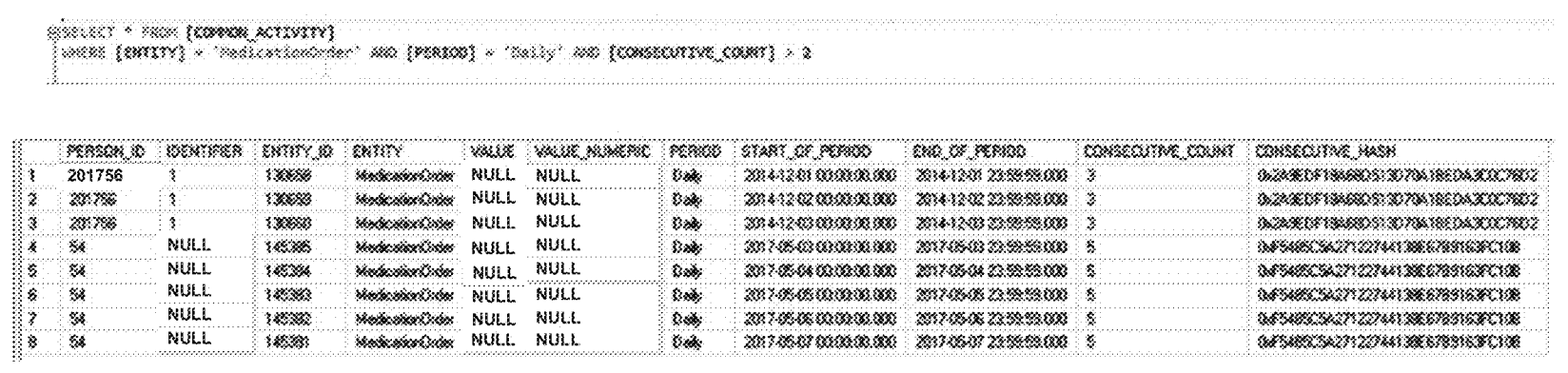

FIG. 21 depicts an example view of a logical database table in a data repository accessible by some embodiments of system 700, as well as an SQL query executed by system 700 to generate the table. As shown, ENTITY_ID links to the medication details for drug 'X', and CONSECUTIVE_HASH is unique for each sequence.

In some embodiments, system 700 is configured to allow the computer to more efficiently evaluate an activity based property when using a timespan. For example, system 700 creates a database view on a data repository where each activity based entity (e.g., drug, surgery, observation, clinical risk, etc.) is stored, along with the timespan period (e.g., hours, days, months, weeks, years), the starting and ending date for the period, and the number of consecutive events (sequences) that occurred for that period. The storage of this type of data in this way allows more efficient evaluation of activity based properties, for example, by reducing the number of tables or computer operations used to access this data at the time an RLQL query 100 is used by system 700 to retrieve corresponding data from the dataset in the data repository. For example, an example of an RLQL query 100 whose retrieval of corresponding data from a data repository by system 700 can benefit from this configuration is "any current inpatient on drug 'X' for more than 2 days".

Figure 22:
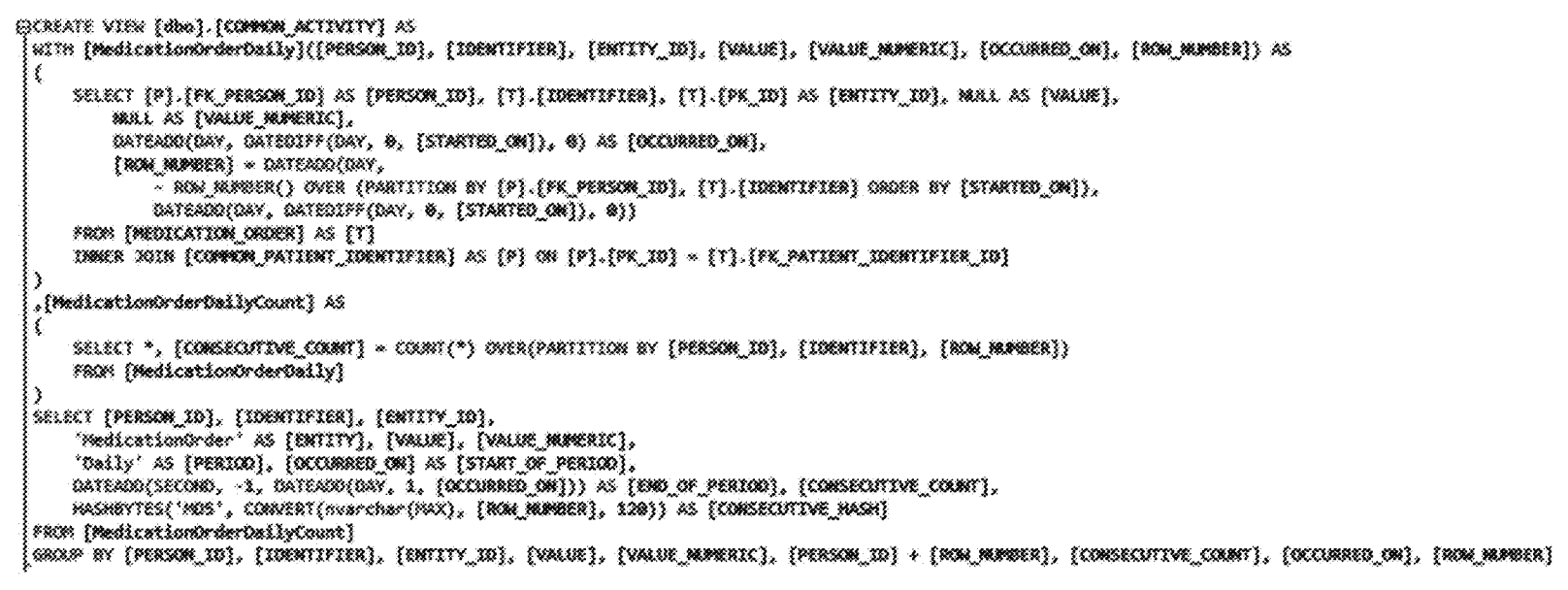

FIG. 22 depicts an example view of SQL code in the activity view for daily medication orders according to some embodiments.

Figure 3:
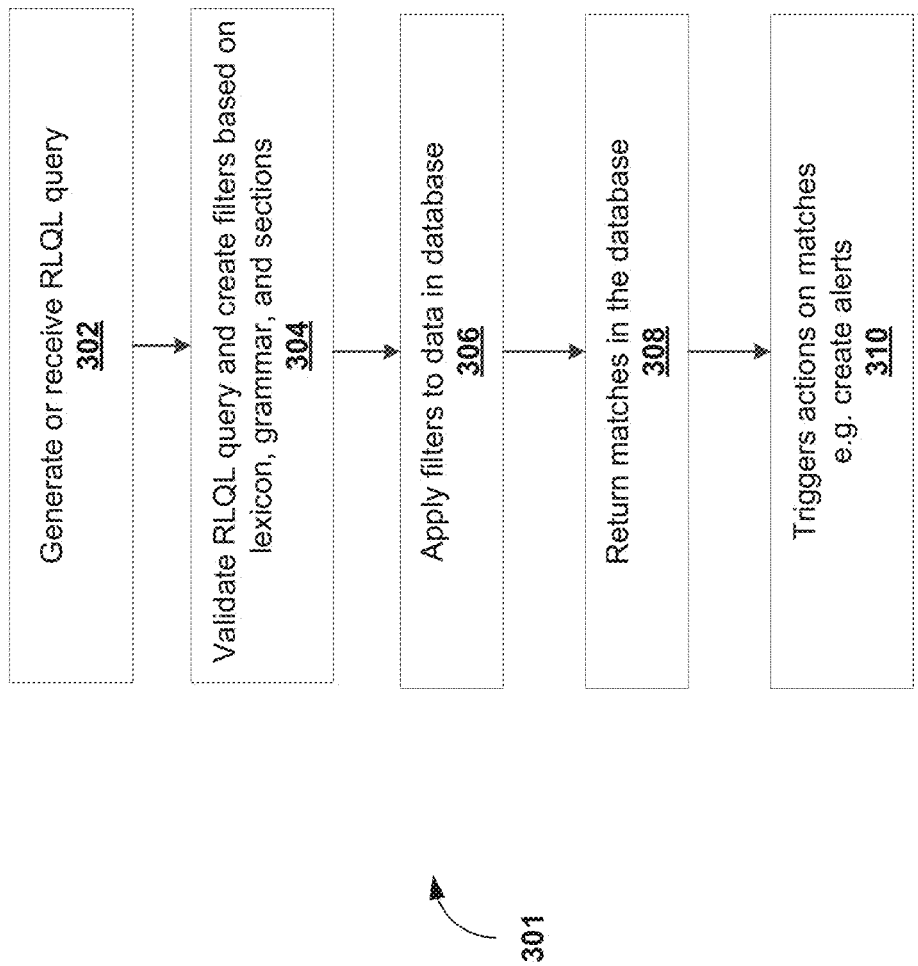
FIG. 3 is a flowchart of a method by a healthcare system, according to some embodiments.

In some embodiments, system 700 is configured to receive RLQL queries 100 that includes one or more timespan filters. Parser 200 identifies the timespan filters and instantiates respective filters 300 with properties or parameters that indicate the data requested in relation to the respective timespan section. For example, in some embodiments, each timespan filter is always associated with at least one other event-based filter (e.g., on drug 'Pen' in the last 2 days). A timespan section can be positioned between two filters (e.g., on drug 'Pen' less than 2 days after having surgery 'Hip') or can be positioned next to another filter (e.g., on drug 'Pen' for more than 7 days in the last 2 months). In each case, system 700 is configured to use the appropriate associated filter(s). Typically this is the event filter positioned to the left of the timespan filter. For example, for the RLQL query 100, any current inpatients admitted in the last 2 weeks on drug 'Pen' less than 5 days after having surgery 'Hip' in the last 6 months, the following would apply:

'in the last 2 weeks' only applies to admission filter
'less than 5 days' applies to both drug and surgery filters
'in the last 6 months' only applies to surgery filter In some embodiments, system 700 applies filters in the order in which the RLQL query 100 is provided, for example, left to right. For example, apart from the initial section, which, in some embodiments, must always be a people section, the sections can be flexibly ordered as each section is processed separately, i.e., converted to a filter if successfully parsed, and the results from each filter are combined when computing for matches. In some cases, for example, location filters, the results of the previous filter are passed to the next filter because, for example, locations are hierarchical in nature, and location values are shared between them. FIG. 3 is a workflow diagram of an example querying process 301 involving system 700 according to some embodiments.

At 302, system 700 is configured to generate an RLQL query 100. In some embodiments, system 700 receives an RLQL query 100 from a user interface portal 102. The user interface portal 102 can include tools used to provide input data used to generate the RLQL query 100, such as values for expressions and the like.

At 304, a parser 200 is configured to validate the RLQL query 100 and parses sections of the RLQL query 100 using the lexicon and grammar. Parser 200 is configured to create one or more filters 300 and/or SQL filters 400 based on the sections of the RLQL query 100. Individual lexical tokens can form the RLQL query 100 and are defined in the lexicon, which contains the complete vocabulary of the DSL code. The lexicon is managed by lexicon evaluating mechanism 210. The lexicon can be used to define the grammar, which defines or groups the words or characters of the RLQL query 100 into discrete sections. Parser 200 uses the grammar to instantiate filters 300 and/or SQL filters 400 based on sections of the RLQL query 100. The filters 300 and/or 400 may be created by the parser 200 to produce results, which may then be filtered against the medical data. Matches may then be acted on, for example, by creating surveillance alerts for data entries that match the RLQL query 100, for example. A database query may be built from the filters 300 and/or SQL filters 400 via SQL builder 600. Each filter 300 and/or SQL filters 400 can have a corresponding SQL class for generating the appropriate SQL query. This may enable or facilitate ad-hoc querying.

RLQL queries 100 enable the use of simple sentence or word based queries to filter complex medical data by creating layer of abstraction from the complexities of SQL based queries. For example, it may be easier to specify whether a user is only interested in current inpatients or in any inpatients or all patients using words or characters particular to an application domain using the DSL code to define the RLQL queries. For example, complex requirements can also be summarised into a simple expression: "any current inpatients with a drug bug mismatch". The corresponding RLQL query 100 will trigger a search for patients who are currently admitted to hospital and have been administered an antibiotic for which they have had a laboratory result showing they are resistant to the prescribed drug. There may also be flexible querying options for timespan. There can be multiple methods for querying by timespans using RLQL queries 100.

For data that supports date time events, an RLQL query 100 can filter based on the following example time based expressions:

Between dates e.g. "patients having surgery 'HIP' or 'KNEE' less than 2 days after being on drug 'AMOX'"
From the current date and time e.g. "patients in unit 'ICU' in the last 2 weeks"
For a given duration e.g. "patients on drug 'AMOX' for more than 2 months"

Embodiments described herein automatically generate or create other language (e.g. SQL) queries from RLQL queries 100 in the DSL code. By abstracting the creation of the RLQL query 100 expressions from the result filter criteria, it is possible to separate the evaluation of matching data from the given expression. This allows any number of interfaces to be implemented. Examples include C# and SQL filtering of data has been written, but it is possible to implement filtering in other APIs and formats.

In some embodiments, a parser 200 is configured to create one or more filters 300 based on sections from an RLQL query 100, where the sections may have been identified using grammar constraints by parser 200. Each filter 300 may be with different concept domains. In some embodiments, each filter 300 is associated with a SQL filter 400. One or more SQL filters 400 is then used by SQL query constructor 500 to create one or more SQL queries (see FIG. 1), which may then be used by system 700 to locate, return, store, and/or transmit data results that are responsive to, correspond to, or match the RLQL query 100 and/or SQL queries.

For example, an RLQL query 100 may comprise the expression "any current inpatient who is in isolation on drug 'levofloxacin' less than 2 days after surgery". When parsed, the input may be broken down by parser 200 so that "any current inpatient" maps to filter 300 PeopleFilter created from section PeopleSection; "who is in isolation" maps to filter 300 PersonFilter created from PersonSection; "on drug 'levofloxacin' maps to filter 300 and/or 400 DrugFilter created from section DrugSection; "less than 2 days after" maps to filter 300 and/or 400 TimeSpanFilter created from TimeSpanSection; and "surgery" maps to filter 300 and/or 400 SurgeryFilter created from section SurgerySection.

At 306, filters 300 and/or 400 are applied to data in one or more databases. For example, in some embodiments, one or more filters 300 may be used by SQL builder 600 to generate a database query. SQL builder 600 may receive a filter 300 or data relating to same, process the filter 300 or the data, and identify, locate, and/or receive an SQL filter 400 that may correspond to, be associated with, or relate to the filter 300. SQL query constructor 500 may then receive one or more SQL filters 400 or data relating to same, process the one or more SQL filters 400 or data relating to same, and generate, construct, or receive one or more database queries. One or more database queries may be executed or performed by system 700 on one or more databases containing, for example, complex patient information and/or records. The one or more database queries may be executed or performed in concert or sequentially to provide efficient return of queried data.

In some embodiments, an order in which one or more filters 300 and/or 400 may be applied to data may be associated with said one or more filters 300, SQL filters 400, and/or a combination of one or more filters 300 and/or 400. In some embodiments, each filter may choose whether to use the unfiltered (original) data source, or the filtered data i.e. the data after one or more previous filters may have been applied. For example, PersonFilter may only filter by timespan on a person with drug bug mismatches and may not filter by timespan for a person in isolation, deceased, age, or sex. In a further example, a timespan occurring before another filter 300 may only be filtered when the timespan is comparing between events in another filter 300, rather than a timespan from the current point in time. That is, TimeSpan may not be applied to filter data and have other filters 300 subsequently applied to data originating from the same RLQL query 100 except when Timespan compares between events in another filter. For example, for an RLQL query 100 "patients on drug 'GENT' less than 2 days after surgery", surgery may not be filtered by the timespan "last 2 days", whereas for an RLQL query 100 "patients on drug 'GENT' less than 2 days after surgery", drugs would be filtered by the timespan "less than 2 days after", which is based on the date of surgery.

In some embodiments, if one or more filter 300 and/or SQL filter 400 such as TimeSpanFilter is used by system 700, system 700 may know about both filters 300 and/or SQL filter 400 DrugFilter and SurgeryFilter in order for the system 700 to perform a many-to-many query between them. For example, system 700 may need to receive and/or use field values and/or lexical tokens relating to DrugFilter and SurgeryFilter. As grammar sections may be flexibly ordered within a RLQL query 100, a single parse using Sprache by parser 200 may not be possible. The system 700 may resolve this by using a fluent interface and method chaining on the infection filters. For example, each filter may inherit from Infection Filter which is position aware, which may allow the parser 200 to perform an exhaustive parse of each filter 300 and/or 400. The exhaustive parse may remove successfully parsed texted from the input expression until the entire expression is parsed or all filters have been attempted.

Events are date based data which occur at a particular point in time. Activities are date based data which have a duration, that is, a start and end date. Activities which have no end date are assumed to still be occurring. The end date can be set as the current date and time. Medications (drugs) may be processed in a similar way.

Figure 10:
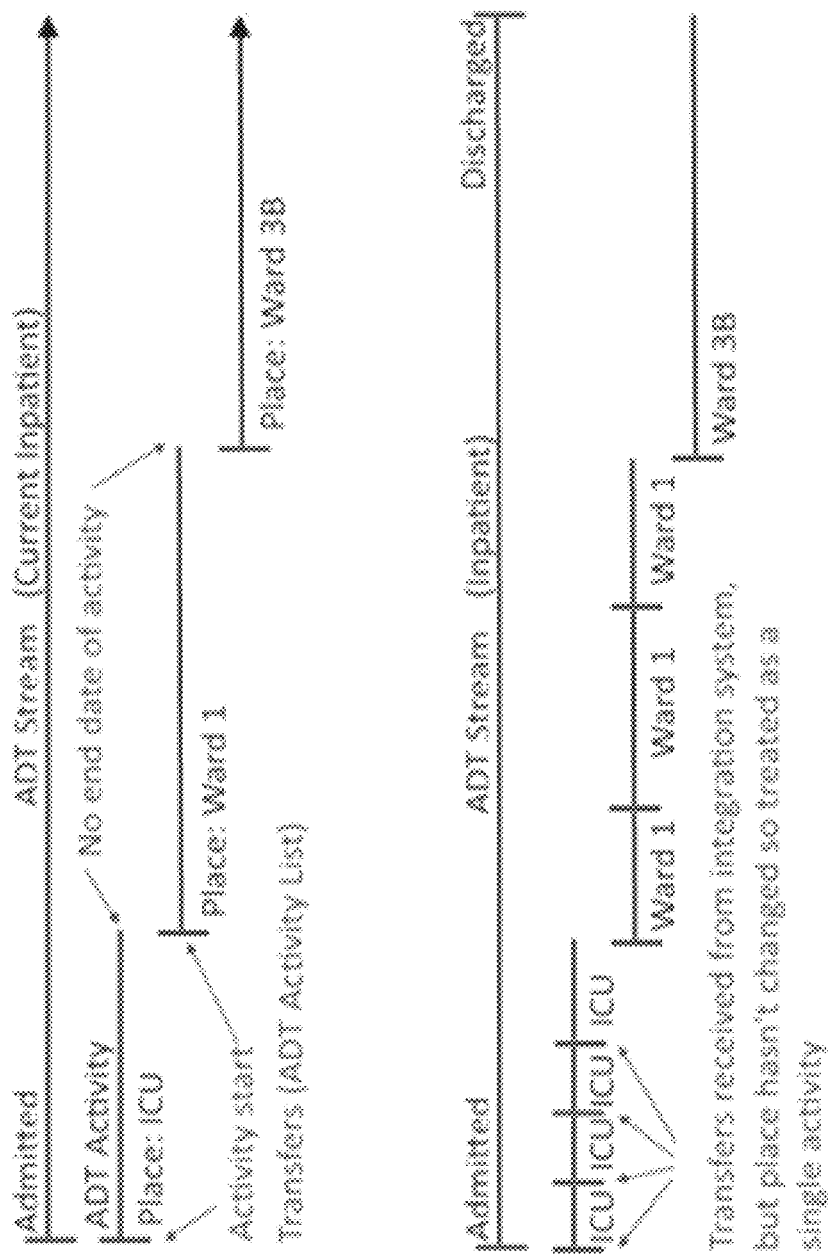
FIG. 10 is a diagram of an admit discharge transfer (ADT) stream for a healthcare system, according to some embodiments.

There may also be location specific timespans in some examples. This may occur where a patient is (currently or historically) located needs to be treated differently than other activity based filters working in conjunction with a timespan filter. The transfer activity might have taken place outside of the range specified, but is valid, because the patient might still be in the location. Transfer activities may not have an end date set, as the end date is inferred when either the patient is transferred to another location or is discharged. However, the end date can be set via AdtActivityList. FIG. 10 includes an example illustration of an admit, discharge transfer (ADT) stream.

In some embodiments, activities are logically distinguished from events during filtering by system 700. This difference is stored by the computer using the domain model used by the filters. System 700 is configured to query the model to determine the type. For activities, system 700 is configured to generate a database view which computes the duration for each period (e.g., hourly, daily, weekly, monthly, yearly) which is used by the SQL filters 400 for SQL code generation.

Figure 11:
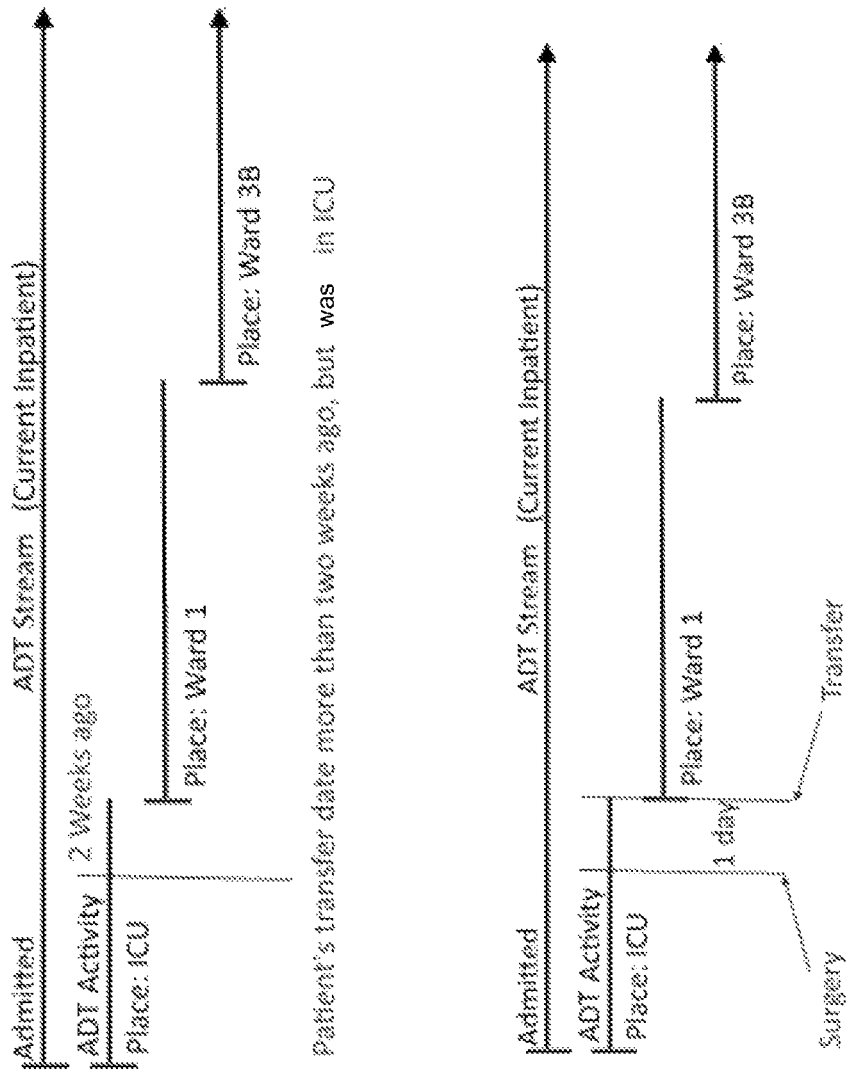
FIG. 11 is a diagram of an ADT stream for a healthcare system, according to some embodiments.

System 700 has to address two different timespan sections in some examples. FIG. 11 shows example illustrations for timespan sections. The first section works against a single filter's 300 events or activities relative to the current date and time, such as "any current inpatient in ICU in the last 2 weeks". The second section works against multiple filters, so instead of being relative to the current date, it can relative to another filter, such as: "any current inpatient in ICU less than 2 days after having surgery". The section "in ICU" can mean currently in ICU or was in ICU at any time in a defined time period (e.g. the last two weeks). This would match if any current inpatient was in, or is still in ICU in the defined time period, for example.

In some embodiments, system 700 may logically organize data into "events" and/or "activities". An event may be date-based data which may occur at a particular point in time. System 700 may associate data relating to a particular point in time to data relating to an event. An activity may be date-based data which may have a duration, that is, a start and end date. System 700 may associate data relating to a duration, for example, by associating data relating to a start date and an end date to data relating to an activity. In some embodiments, an activity that may not be associated with an end date may be assumed to still be occurring. In that case, system 700 may associate and/or set an end date with the activity as the current date and/or time. System 700 is configured in these embodiments to store such associations in a data structure, for example, a database whose values can be queried.

At 308, data matching or corresponding to the queried data may be identified, located, processed, combined, decompressed, and/or returned by system 700.

In some embodiments, data matching or corresponding to the RLQL query 100, SQL query, and/or database query may be updated, changed, deleted, moved, combined, and/or associated with other data. In some embodiments, the data may be patient information and/or patient records; data relating to or associated with same; data stored in, received by, transmitted from system 700; and/or data relating to lexicon, grammar, and/or definitions of what parser 200 may receive, process, and/or parse. In this way, a query may be provided to, generated by, and/or used by system 700 that enables the modification of the RLQL syntax, the storage structure of or organization of data in one or more underlying databases, for example, for increased efficiency of system 700 and return of queried data; for creating, deleting, or modifying definitions of grammar, lexicon, sections, filters 300 and/or 400, database fields, associations between same, and/or enumerations between same.

At 310, system 700 may act on data returned by system 700 and/or the return of data by system 700 may trigger one or more events. For example, an alert may be created and associated with the returned data or the RLQL query 100, SQL query, and/or other database query leading to the return of the data may be stored and/or transmitted. Said query or queries may be executed or performed subsequently by system 700 according to time, for example, at regular subsequent intervals, at time of subsequent request, and/or when additional data is stored in or received by system 700 or one or more databases associated with system 700. This may allow for one or more queries to be executed upon receipt by system 700 or one or more databases associated with system 700 of data relating to a pertinent patient-related incident, for example, a complex medical event, and for a health care professional to be alerted immediately. The alert may be delivered in the form of an electronic alert notification with a message and recipient.

In some embodiments, the user experience provided by system 700 may include a computing tool for rule configuration that may assist a user with constructing RLQL queries or engaging with the system 700 or any of its components, such as the SQL builder or search functionality. For example, a computing tool for rule configuration may provide visual, audio, or other tips, informational visual overlays, audio cues, connectivity to specific locations on the Internet or to external sources from which guidance may be derived. The computing tool for rule configuration may enhance and/or assist with the enhancement of the ease and/or efficiency with which the system 700 is used and/or data is found in the database.

In some embodiments, the user experience provided by system 700 may include an "auto complete" functionality that assists with, suggests, and/or rewrites user input. The "auto complete" functionality may enhance and/or assist with the enhancement of the ease and/or efficiency with which the system 700 is used and/or data is found in the database.

In some embodiments, the system 700 may include functionality to store, receive, transmit, and/or record patient records or data relating to one or more patients. In some embodiments, the system 700 may include functionality to report data relating to RLQL queries 100, one or more patients or patient records, one or more filters 300, one or more SQL filters 400, SQL query constructors 500, parsers 200, and/or associations between one or more components of the system 700 or data stored, received, transmitted, and/or recorded involving the system 700. Such reporting may be to hospitals, research facilities, health care professionals, and/or other systems 700.

RLQL queries 100 may be used to query all patients in one or more databases for one or more hospitals using an infection surveillance application rendered as part of user interface portal 102. System 700 can implement an infection surveillance that integrates with the infection surveillance application. An RLQL query 100 may be for an individual patient in the infection surveillance application. An RLQL query 100 may be used to create and manage surveillance alerts based on data stored in one or more databases associated with system 700. An RLQL query 100 may be used with a surveillance reporting engine and in facilitating the display of patient records and/or data relating to one or more patients.

A user engaging with system 700 may search one or more associated databases by providing a patient name, an identifier, and/or an RLQL query 100. An example workflow may comprise the following steps.

In some embodiments, system 700 implements the following additional features and corresponding improvements or advantages to computer functionality.

A) Added ability to filter (exclude) patients by their location with respect to the scope of the user executing the RLQL query. For example, a user may only be scoped to view facility A, but there are matching events in both facility A and B. In some embodiments, system 700 is configured to not evaluate the events in facility B when deciding if the patient matched the RLQL expression. Similarly, if all locations in the RLQL expression are within scope for the user executing the search, system 700, in some embodiments, is configured to generate SQL code that excludes the location scope check from the SQL query. This reduces the amount of time it takes to execute the query on the database server.

B) Simplified code generation for SQL anti-infective filter when mapping WHO ATC classes against anti-infectives specified in RLQL. In some embodiments, system 700 is configured to generate an SQL query including only a single table join in place of multiple table joins. The reduction in joins improves performance during query execution.

C) Consistency in logic used for retrieving data from a data repository given an RLQL query 100. For example, in some embodiments, a system 700 is configured to implement a person filter 300 and drug bug detector so they use the same code for detecting when a patient is administered a drug that they have previously been tested as having an organism they are resistant to. i.e. a "drug bug mismatch". This ensured that the same logic is consistently applied.

Figure 4:
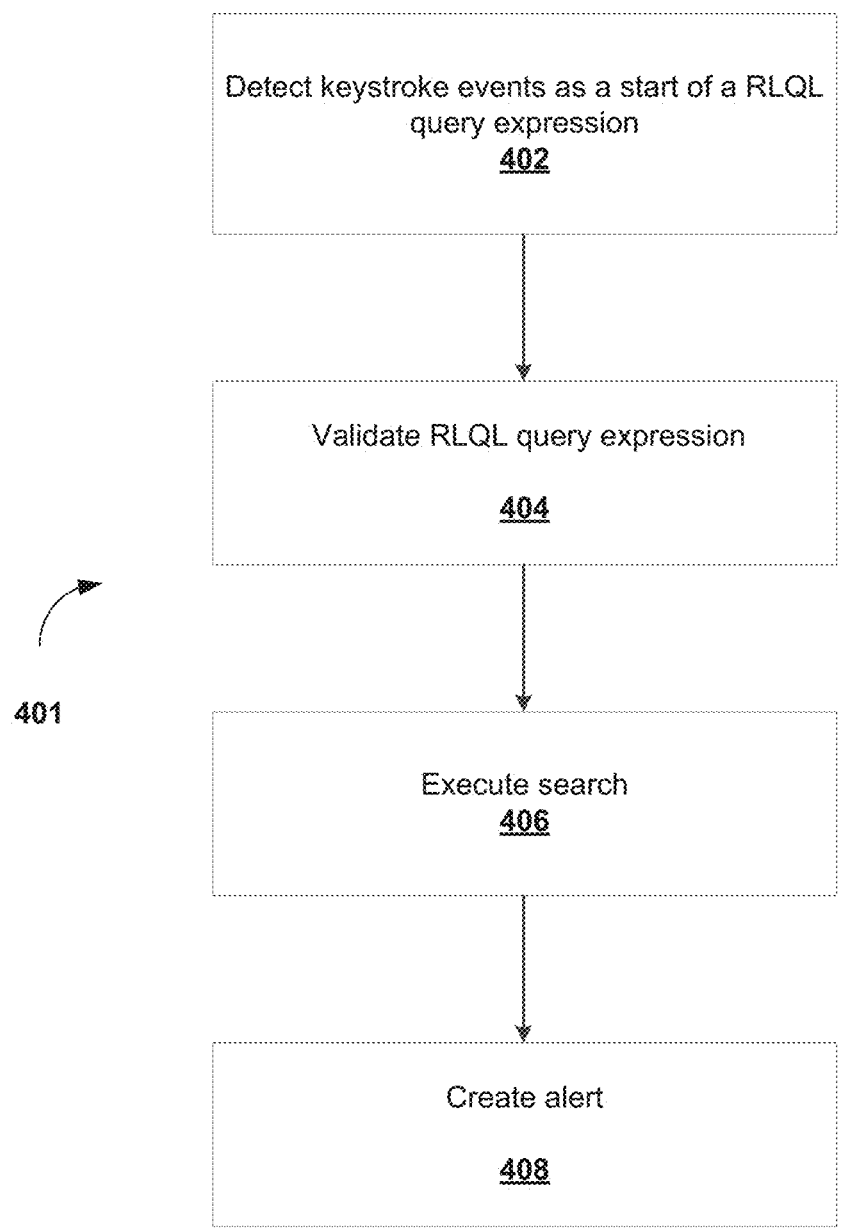
FIG. 4 is a flowchart of a method by a healthcare system, according to some embodiments.

FIG. 4 is a flowchart of a method 401 for querying, transforming and displaying medical data from persistent data stores using a domain specific language for a medical application domain. At 402, system 700 detects keystroke events as a start of a RLQL query 100 expression at user interface portal 102. An RLQL query 100 can also be referred to as a medical query. At 404, system 700 validates the RLQL query 100 expressions. At 406, system 700 executes a search of databases using the RLQL query 100. At 408, system 700 creating a surveillance alert based on the medical query expression.

Figure 5:
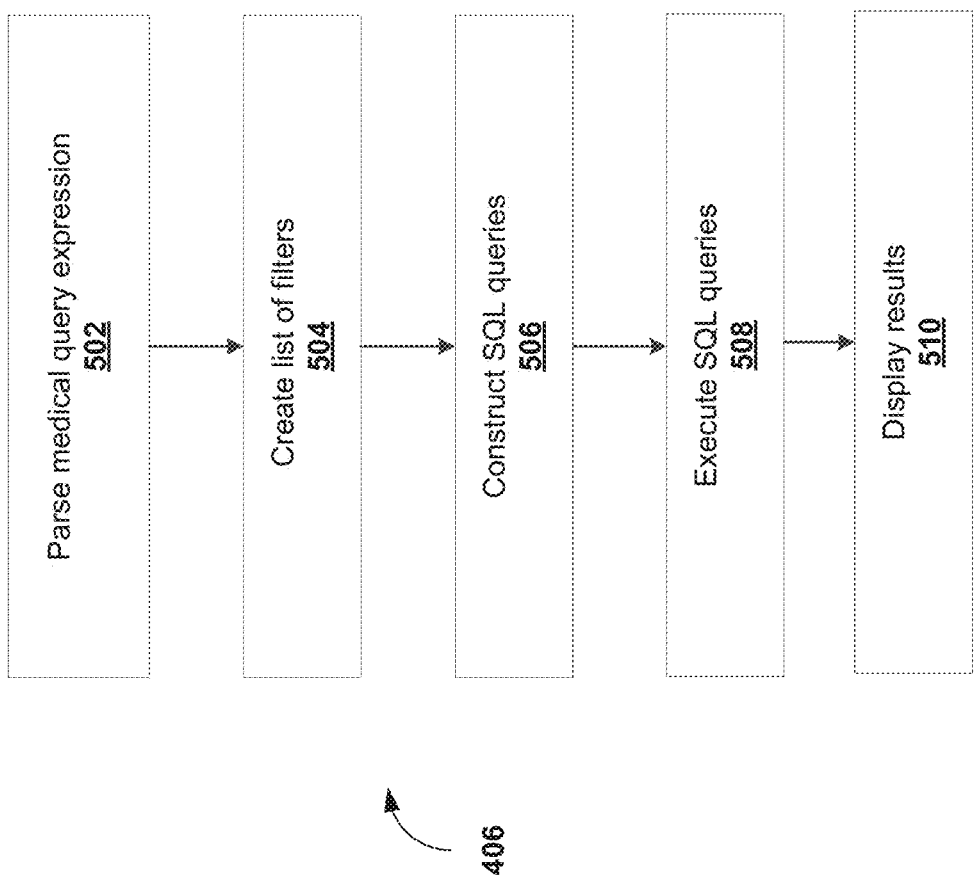
FIG. 5 is a flowchart of a method for executing searches by a healthcare system, according to some embodiments.

FIG. 5 is a flowchart of a method for executing a search of databases using the RLQL query 100. At 502, system 700 parses the RLQL query 100 expression into sections. At 504, system 700 creates a list of filters for the sections of the RLQL query 100. At 506, system 700 generates an SQL query using the filters and sections of the RLQL query 100 expression. At 508, system 700 executes the SQL query against one or more databases to retrieve a list of matching patient identifiers. At 510, system 700 generates visual elements for the user interface portal 102 corresponding to the list of matching patient identifiers and a results summary. The user interface portal 102 and system 700 can receive commands based on the visual elements to trigger actions, such as alert creation, further RLQL queries 100, and data modifications.

As noted, at 402, the system 700 detects keyboard events. If an RLQL query 100 expression input is detected, for example, by matching the input with the start of an RLQL query 100 expression, the input is parsed by system 700 for validity. Terminology entered into a RLQL query 100 are identified and mapped to associated concepts and descriptions.

If a valid RLQL expression is entered, the user may be permitted by system 700 to execute a search (406) based on the RLQL query 100 and create a surveillance alert (408).

A user may request the execution of a search using a command received at user interface portal 102. If a search is executed at 406, a parser 200 creates a list of filters 300 (at 504) with the appropriate criteria and/or fields for each of them, based on the RLQL query 100 expression 100.

For each filter 300, an SQL builder 600 creates an SQL filter 400. SQL builder 600, for example, using SQL query constructor 500, constructs an SQL query at 506. The SQL query is executed at 508 against one or more databases associated with system 700, which returns a list of matching patient identifiers as results, as well as patient details and other related data. The system 700 may display a summary of the search result as visual elements that are part of user interface portal 102, as well as patient details, and/or other data from one or more associated databases.

Figure 6:
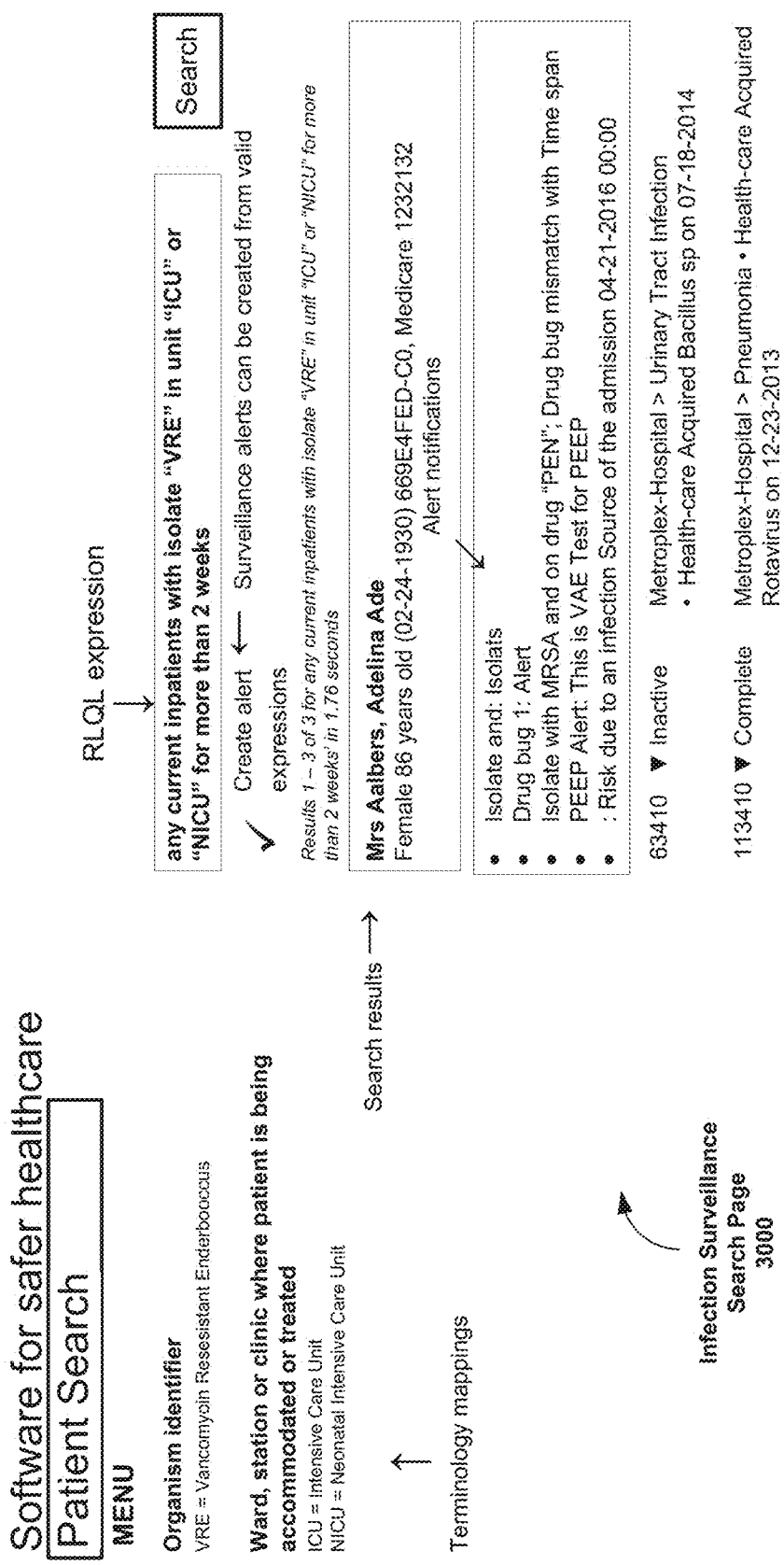
FIG. 6 is a screenshot of an interface for a healthcare system, according to some embodiments.

FIG. 6 is a diagram of an example infection surveillance search page 3000 that may be rendered on user interface portal 102. The search page may include a portion for display of information, such as definitions of terminology; a portion where an RLQL query 100 expression may be provided as input; a button to trigger creation of a surveillance alert; and a portion to display search results and/or data returned by a RLQL query 100, SQL query, and/or database query. The page 300 may also show previous RLQL queries 100 along with a status identifier, such as inactive, complete.

A user engaging with system 700 may query for an individual patient using an RLQL query 100. For example, in the infection surveillance application of user interface portal 102, a user may view all details on patient events and activities, as well as execute an RLQL query 100.

Another example workflow may comprise the following steps. The system 700 may detect keyboard events at 402. If an RLQL query 100 expression input is detected, for example, by matching the input with the start of an RLQL query 100 expression, the input is parsed by system 700 for validity at 404. Terminology entered into a query are identified and mapped to associated concepts and descriptions. If a valid RLQL expression is entered, the user may be permitted by system 700 to execute a search (406) and create a surveillance alert (408).

Data for the patient model may already be loaded in some example embodiments. Once the RLQL expression is successfully parsed, the filters 300 can be evaluated to determine if the patient matches the expression. Once the filter result is known, the page 3000 is updated to display whether the patient matches the expression as results.

Figure 7:
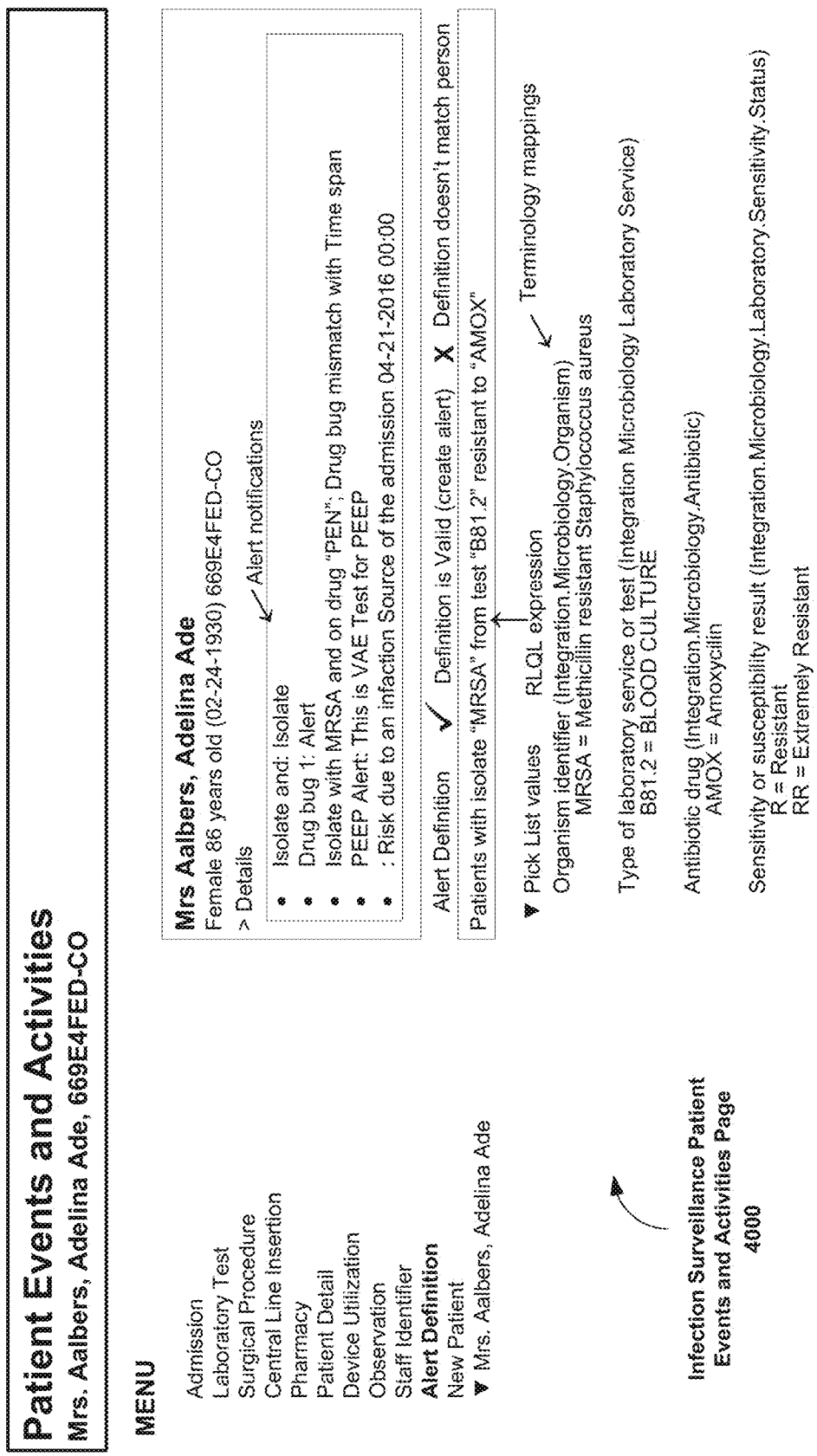
FIG. 7 is a screenshot of an interface for a healthcare system, according to some embodiments.

FIG. 7 is a diagram of an example infection surveillance patient events and activities page 4000. The page 400 can be rendered on user interface portal 102. The page can include visual elements for depicting various features, including alert notifications, RLQL query 100 expressions, terminology mappings, and so on. The page 400 may be part of an alert definition feature of system 700. The page 400 may also include an indication that the RLQL query 100 expression is valid and results returned by executing the search.

A user engaging with system 700 may create surveillance alerts. For example, a surveillance alert may use a scheduler to determine how frequently an alert is evaluated, when an alert is triggered, and to whom alert notifications should be sent.

A user engaging with system 700 may create a surveillance alert from an infection surveillance search page 3000 rendered by user interface portal 102, an individual patient events and activities page 4000, and/or from an alert management form.

An example workflow comprises the following steps. When system 700 detects an alert schedule is ready to execute (e.g. by a schedule or timing property of the alert definition), system 700 instantiates a surveillance alert, passing along the alert details for evaluation, which include the RLQL query 100 expression (alert definition). The RLQL query 100 expression is then parsed for validity (502), and if valid, a list of filters 300 is created (504). For each filter 300, an SQL builder 600 creates an SQL filter 400. SQL builder 600, for example, using SQL query constructor 500, creates an SQL query (506). The SQL query is executed against one or more databases associated with system 700, which returns a list of matching patient identifiers to populate pages rendered by the user interface portal 102.

For all matching patients, criteria for all filters 300 are hashed and then compared against a list of existing hashes for the alert notification and transmission to the recipient. If the hash is a match and it is not a repeat alert, then the alert notification is not triggered as a previously executed alert schedule has already triggered the alert notification. This may help avoid repeated alerts for the same recipient and trigger. The alert notification is then triggered. The alert notification can be sent via email or added to the alert notification widget. The filter criteria hash is added to the list of existing hashes to avoid unwanted re-triggering of alert notifications. Hashes may be conducted using hash techniques such as MD-5, SHA, among others. Hash values may be stored as a separate column or data value field in the underlying data storage, or in the form of a separate hash table (e.g., a two dimensional hash table, storing a latest hash value alongside identifiers). Every time a new query is run, a hash value may be taken of the data set that was analyzed for the user, and the generated hash may be compared against the stored hash value to check to see if the data for the user has changed since the last query. If the hash has not changed, the data has not changed and accordingly, an alarm or notification trigger state should not be toggled.

FIG. 8 is a diagram of an example creation of an alert creation form from an infection surveillance search page 5000. The alert can include different properties including alert type and alert definition. The alert definition can be defined using an RLQL query expression. The alert can also include recipient, message and contents for the alert notification. The alert can also include schedules or timing data for its evaluation.

Embodiments described herein may provide a simplified querying language for infection surveillance. An RLQL query 100 can use simple sentences to filter complex data. For example, it may be easier to use an RLQL query 100 than some other query languages to query current inpatients, any inpatients or all patients. Complex requirements may also be summarized into a simple expression, for example, "any current inpatients with a drug bug mismatch". In another example, RLQL query 100 and system 700 may allow searching for patients who are currently admitted to hospital and have been administered an antibiotic for which they have had a laboratory result showing they are resistant to the prescribed drug.

System 700 may provide multiple methods to query data relating to timespans. For example, for data that supports date time events, a user may filter: between dates, for example, "patients having surgery 'HIP' or 'KNEE' less than 2 days after being on drug 'AMOX'"; from the current date and time, for example, "patients in unit 'ICU' in the last 2 weeks"; and for a given duration, for example, "patients on drug 'AMOX' for more than 2 months".

System 700 may allow any number of user interfaces and/or query languages to be associated with same. For example, system 700 may abstract and/or separate the creation of an RLQL query 100 from the result filter criteria and separate the evaluation of matching data from the given RLQL query 100. For example, in some embodiments, an SQL builder 600 may create an SQL query from an RLQL query 100 provided by a user to a form presented by form engine 910. In some embodiments, C#, SQL, or other APIs and formats may be used to filtering data stored in one or more databases associated with system 700 in response to an RLQL expression.

In some embodiments, system 700 may be used to support a pharmacy application. An example workflow for a pharmacy project may include initial acknowledgement; 72-hour check-in; patient concern resolved; and patient concern resolved (call center). The workflow may be implemented through use of database fields to store different acknowledge related values. Query expressions may be used to pull data from these fields and compute the information required for the workflow. System 700 may be able to support the workflow.

An RLQL query is constructed using a domain specific, user-friendly language that may allow clients to query medical information, for example, drugs, lab results, observations, locations, clinical risks, and surgery, stored in one or more databases and to create their alerts and messaging rules based on those queries. For example, clients may search for: "any patient with clinical risk 'EBOLA'"; "any inpatient on drug 'VANC' and younger than 10 years"; "any current inpatient in unit 'ICU' or 'NICU' for more than 48 hours"; and "any inpatient with isolate 'MRSA' on drug 'GENT' less than 2 days after surgery".

Implementation of system 700 may separate the server-side and client-side code to make it easier and faster to modify the design of the application. In some embodiments, implementation of the user interface portal 102 can render forms and other pages. Separation between the back-end and front-end of the application may be enhanced by using APIs to assist with communication between the back-end and front-end and/or use of a single-page Application (SPA) using Ember.js front-end framework. REST APIs may be used to facilitate communication between the front-end, back-end, and one or more databases.

Figure 9:
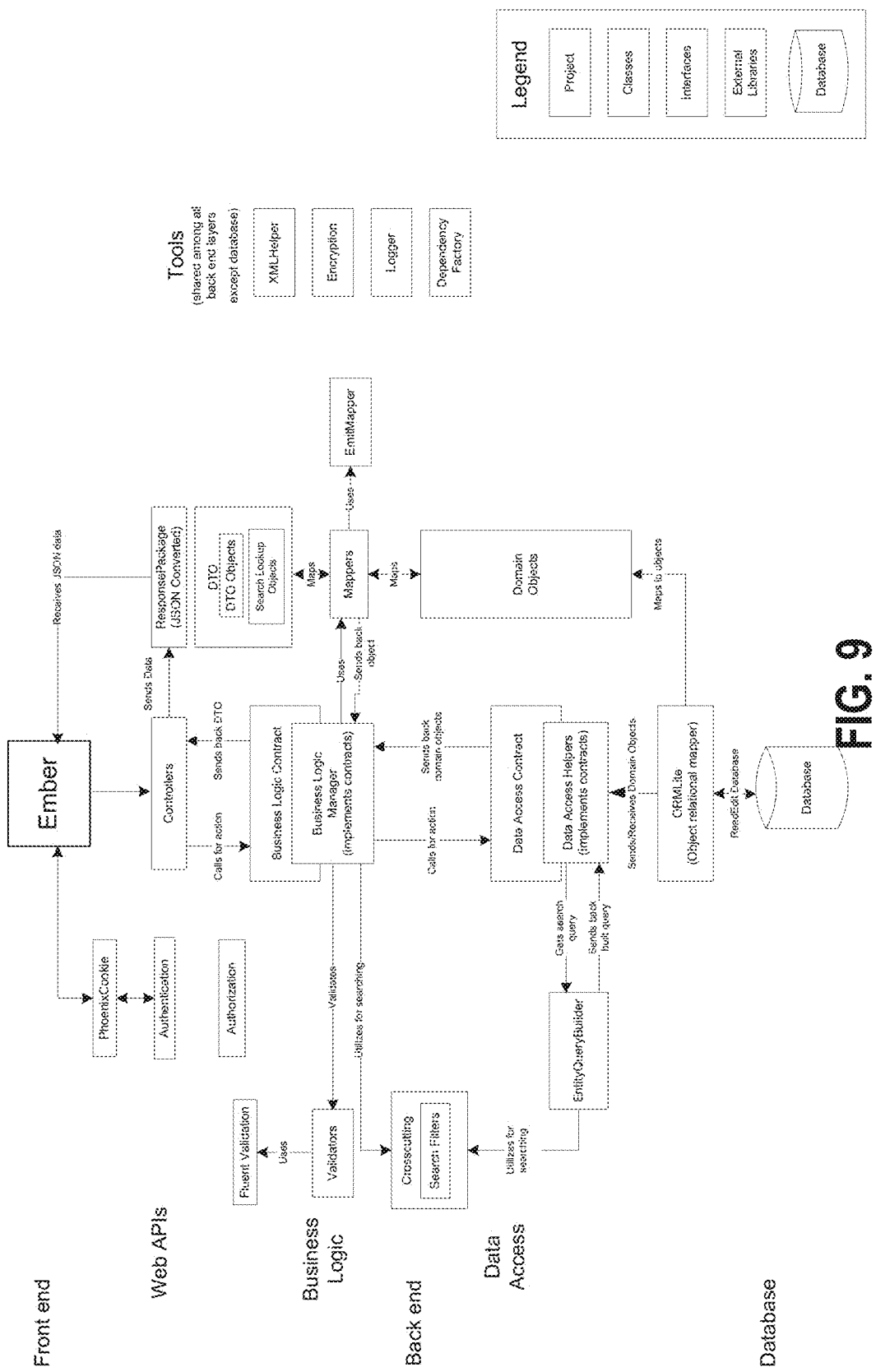
FIG. 9 is a schematic diagram of a healthcare system, according to some embodiments.

FIG. 9 is a diagram of an example implementation 6000 of system 700. For example, domain classes and domain objects may be employed. Domain objects may be an exact representation of a table within the database. Within each class, domain objects contain a schema and corresponding alias which marks their name in the database. In addition, domain objects may have properties which are marked with their own alias. Domain objects may provide a direct mapping to the actual column in the database.

System 700 may use data transfer object (DTO) classes and DTO objects. DTO objects may hold data that the front-end needs, sends, and/or requests. DTO objects may hold a representation of what is on the front end. Most fields may be mapped one to one with domain objects but DTO objects may have certain fields that may be filled in with custom logic and/or be implemented from other domain objects. For example, a User DTO object may have all of User Domain fields and assignment fields which is a separate domain object from Users.

System 700 may use lookup classes. Within a search or an inbox, it may be unnecessary to send back a collection of DTO objects with every property. Lookup classes may be a subset of each DTO which may be more lightweight than the actual DTO object. In addition, a lookup class may contain properties that only exist in search that do not exist in DTOs.

System 700 may use mapper classes. Mappers may be used to map Domain objects to DTOs and vice versa. Domain to DTO mapping may be used to enable a controller to return information to a user. DTO to Domain mapping may be used to save and/or update information, data stored in a database, dataset associated with a file, and/or one or more files.

System 700 may include an authentication component. An authentication component may process login and logout requests by one or more users. An authentication component may process, save, store, and/or transmit a client and/or user's cookie which may contain a set of information and/or data that may be used by system 700 to identify the client and/or user's session.

System 700 may use controllers, for example, API controllers. An API controller may contain corresponding methods to retrieve information and/or data from one or more databases, contain appropriate HTTP methods for REST, and make method calls to authorization to check whether an associated user engaged with system 700 has permissions to use a specific method.

In some embodiments, system 700 may use a class called ResponsePackage which may contain and/or specify the type of information the system 700 may send to Ember, the object that may be sent to Ember, and the object's meta data. system 700 may convert data sent to Ember, for example, said information, object, and data to JSON using an external library: Newtonsoft JSON.

A controller method may have an authorization attribute called AuthorizeUser which may immediately check if a user engaged with system 700 has permission to utilize a certain call to the controller.

In some embodiments, system 700 may use a Business-Logic layer. A manager may be used to handle all of the data manipulation that may be needed for a specific action in the controllers. A manager may retrieve data from a database, process the data, and convert the data and/or processed data into a DTO object for a controller to send back to Ember.

In some embodiments, system 700 may use interfaces (including an interface for user interface portal 102). Each manager may have its own interface which it may implement. A dependency factory may inject the program with an actual class. Any files that need to refer to a manager class will use the interface instead of instantiating the actual class.

In some embodiments, entities, objects, and/or classes may have an associated validator which may check whether the data that is being created, updated, deleted, and/or used by the entity, object, and/or class is valid. The validators may use an external library called FluentValidation. Validators may check data using set of developer created rules. These rules may be used to check whether the properties in the entity are valid and may generate alerts and/or feedback based on the checking.

In some embodiments, system 700 may use a DataAccess layer, for example, comprising ORMLite that may map one or more tables in one or more databases to specific domain objects. ORMLite may contain features that may be performed directly in an SQL query for example, join clauses, where clauses, and order by clauses. ORMLite may retrieve data from one or more databases by generating one or more query strings during runtime and requesting the data using the query.

A DataAccess layer may include data access helpers may be used to return an actual object from a specific table. Data access helpers may create queries to return an object in a specific manner. For example, a data access helper use ORMLite to inner join multiple tables together to return a specified table.

In some embodiments, queries may be hard coded by prepending and appending part of an SQL statement and/or query in one or more strings. This may enable the execution of complex queries that may not be processed by ORMLite.

For example, the searching query in ORMLite has complex logic to build a complex query. In some instances, there may be several simple queries created to formulate a complicated query. In order to join these simple queries together, it is may be necessary to hard coded the corresponding SQL string.

In some embodiments, system 700 may support crosscutting functionality. Crosscutting functionality may encompass use of classes across multiple layers in the project. For example, when searching for entities a user may engage with the front end and apply certain filters that may limit information returned. The front end may pass data and/or properties to a controller which may then process the data and/or properties using a SearchFilter. A SearchFilter may contain multiple properties that control what is sent back to the front end. For example, to control page size, a user may specify the page size property, a filter may set the page size property, and ORMLite may return the correct amount of entities requested.

In some embodiments, system 700 may support a tool functionality. Tools functionality may encompass a set of static classes and methods that may be used across an application, system 700. For example, method XmlHelper may be called to parse an XML string and returns its attributes; method StringHelper may be called to turn strings into a specific format, for example, CamelCase or pluralized forms of a provided string; and method Logger may be called may create one or more logs of actions performed by system 700 as a program runs.

Figure 12:
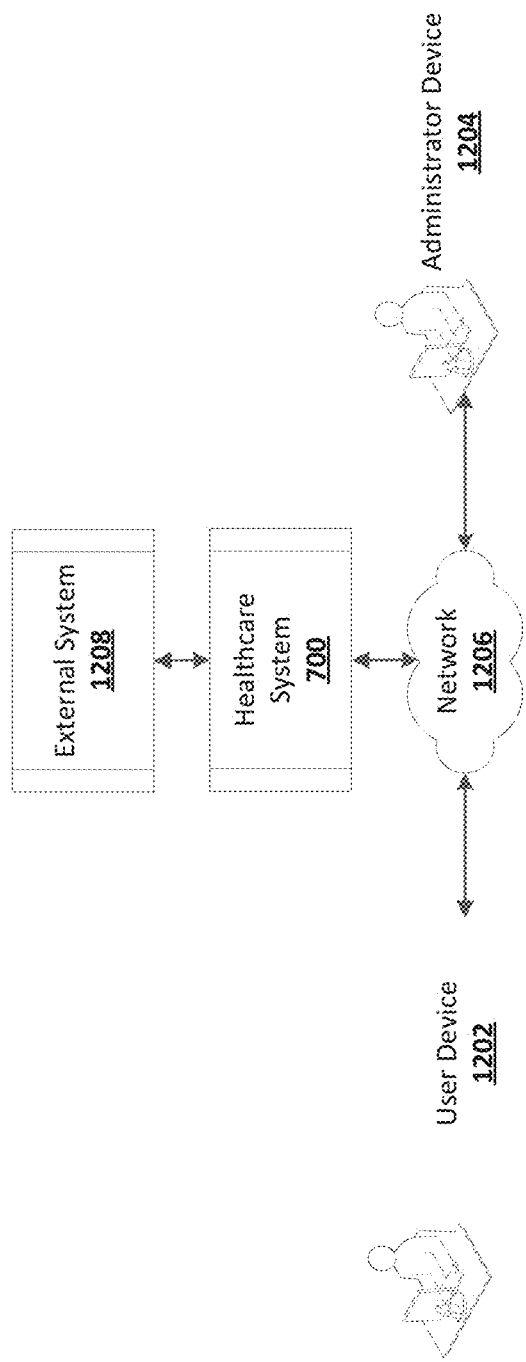
FIG. 12 is a schematic diagram of an environment for a healthcare system, according to some embodiments.

FIG. 12 is a diagram of an example environment for system 700 according to some embodiments.

Healthcare system 700 can be part of an integrated system for implementing different functionality in addition to the RLQL query 100 generation and execution described herein. Healthcare system 700 provides an infrastructure for configuration and implementation of sequences of tasks for one or more health care facilities, where the sequences of tasks are arranged as workflows. The tasks may relate to creating or updating healthcare data files, transmitting messages and alert notifications, executing routines, activating hardware components such as data capture devices, validating data, and so on. Healthcare system 700 implements different workflows for different types of jobs or processes. Healthcare system 700 assigns different devices or users different tasks of the sequences of tasks defining the workflows. Once a task is complete, healthcare workflow system 700 implements other tasks based on the sequences of tasks for different workflows. The sequences of tasks may have complex dependencies involving different devices and users.

Healthcare system 700 couples to user device 1202 (with user interface portal 102) rendering a form to receive or transmit healthcare data by form fields to activate workflows or as part of a task for a workflow. The form can generate pages for RLQL queries 100 and alert configurations, as described herein. Healthcare system 700 couples to administrator devices 1204 via network 1206 to receive or transmit healthcare data and RLQL queries, and configure rules or alerts for workflows to create or update tasks, for example. Healthcare system 700 also connects to external systems 1208 (with one or more databases) to receive or transmit healthcare data to implement or activate workflows and tasks. Healthcare system 700 can execute RLQL queries 100 on local databases or external databases on external systems 1208.

Healthcare system 700 connects to other components in various ways including directly coupled and indirectly coupled via the network 1206. Network 1206 (or multiple networks) is capable of carrying data. Network 1206 can involve wired connections, wireless connections, or a combination thereof. Network 1206 may involve different network communication technologies, standards and protocols, such as for example Global System for Mobile Communications (GSM), Code division multiple access (CDMA), wireless local loop, WMAX, Bluetooth, Long Term Evolution (LTE) and so on. Network 106 may involve different physical media such as coaxial cable, fiber optics, transceiver stations and so on. Example network types include the Internet, Ethernet, plain old telephone service (POTS) line, public switched telephone network (PSTN), integrated services digital network (ISDN), digital subscriber line (DSL), and others, including any combination of these. Network 106 can be a local area network or wide area network.

Figure 13:
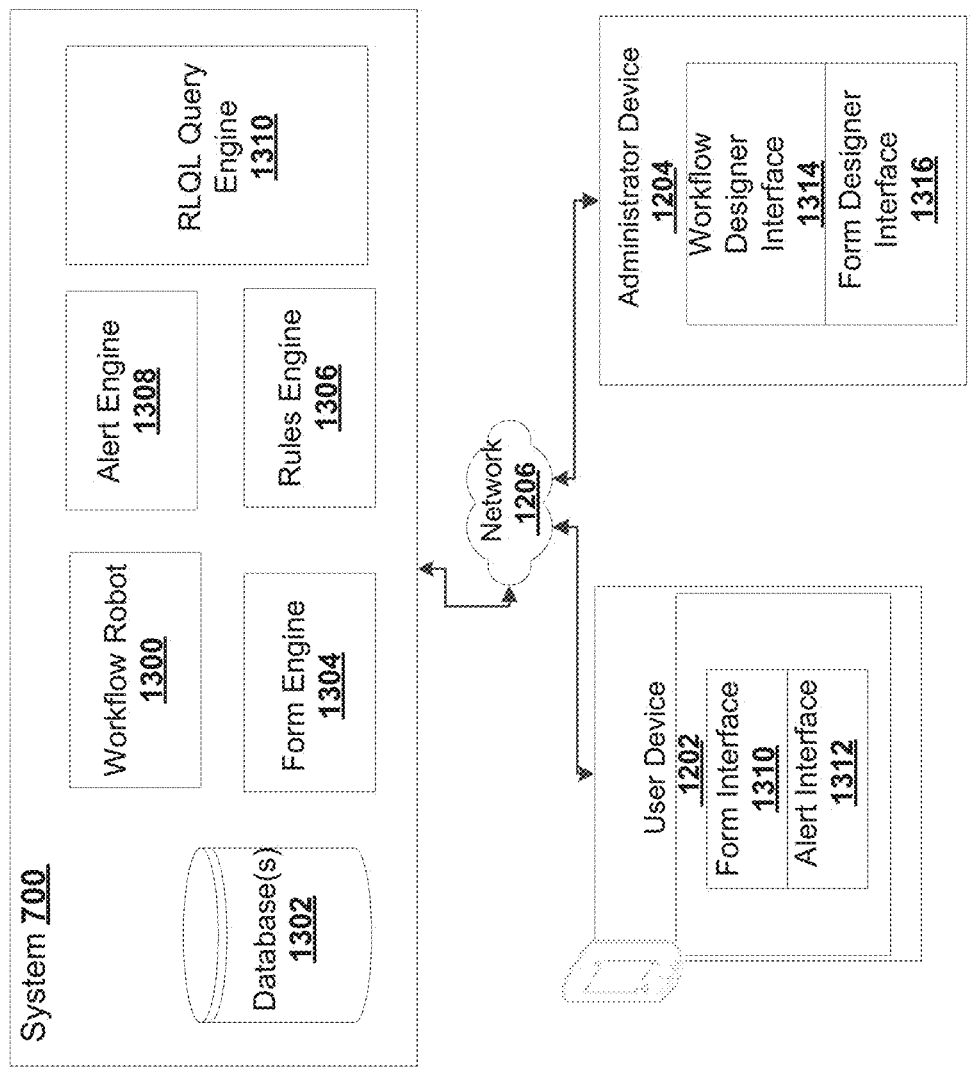
FIG. 13 is a schematic diagram of a healthcare system, according to some embodiments.

FIG. 13 is a diagram of another example healthcare system 700 according to some embodiments. Healthcare system 700 can implement aspects of the infection surveillance system described herein, using workflows, rules, alerts and RLQL queries.

Healthcare system 700 has a database 1302 storing healthcare data, rules, an event queue of event entries, rules, and other data. Healthcare system 700 has a workflow robot 1300 which is a virtual agent implemented by a computing device guided or instructed by rules. The workflow robot 1300 evaluates and executes rules to automatically implement workflows for one or more healthcare facilities. The workflows can modify data in database which is queried using RLQL queries 100. Healthcare system 700 has a rules engine 1306 to create and manage the rules, which can be used as part of alerts and RLQL queries 100. Healthcare system 700 interacts with workflow designer interface 1314 on administrator device 1204 to create and update rules, alerts and RLQL queries 100 using visual elements rendered as part of the workflow designer interface 1314. The workflow designer interface 1314 generates visual elements for creating, modifying and deleting rules and provides rule configurations to the rule engines 1306 to create, modify and delete rules in the database 1302.

Healthcare system 700 has a form engine 1204 that interacts with a form interface 1310 to render forms having form fields and corresponding form field values to receive and transmit healthcare data. Forms can be used to populate user interface portal 102, and in particular, forms can be used to receive RLQL queries 100. User interface portal 102 renders form interface 1310 and alert interface 1312 to receive RLQL queries 100. The form interface 1310 creates or updates healthcare data in database 1302. Modifications, deletions and additions to the healthcare data in database 1302 are events that activate the workflow robot 1300 to evaluate and execute rules for automatically implementing the workflows for healthcare facilities. The workflows may relate to RLQL queries. The form engine 1304 interacts with a form interface designer interface 1316 to create, customize and configure forms (and form fields) rendered by the form interface 1310. A customized form may include one or more form fields for receiving RLQL queries.

The rules engine 1306 or form engine 1304 detects events based on received or updated healthcare data from the form interface 1310 or RLQL queries 100 received from the form interface 1310. The rules engine 1306 or form engine 1304 stores event entries for the detected events to an events queue stored in database 1302. The event entries include data indicating changes that have been made to files and/or non-file-related actions. The workflow robot 1300 activates when the event entries are stored to the events queue or upon expiration of a timer, for example. The rules engine 1306 identifies a set of rules stored in the database 1302 in response to activation of the workflow robot 1300. Each rule has a trigger and an action relating to the healthcare data in the database 1302. The workflow robot 1300 iterates the set of rules to evaluate the trigger of each rule for execution of the action of the rule based on the event entries.

Healthcare system 700 has an alert engine 1308 to transmit alert notifications to an alert interface 1312 on user device 1202 when implementing the workflows. The alert engine 1308 manages alerts that may be defined based on results of RLQL queries as described herein. The alert engine 1308 facilitates the generating of alerts and notifications based on defined alert or schedule expressions and actions of rules. The alert engine 1308 engages a scheduling service that periodically runs and scans the database for matching alerts. For example, scans can be run on an hourly or daily basis for performance reasons. However, manually entered RLQL expressions in the search query or patient details page trigger (near) real-time searching of the current database state in (near) real-time, which can also be used for alerts. Further details are provided in U.S. Provisional Application No. 62/353,707 filed Jun. 23, 2016 the entire contents of which are hereby incorporated by reference.

The embodiments of the devices, systems and methods described herein may be implemented in a combination of both hardware and software. These embodiments may be implemented on programmable computers, each computer including at least one processor, a data storage system (including volatile memory or non-volatile memory or other data storage elements or a combination thereof), and at least one communication interface.

Program code is applied to input data to perform the functions described herein and to generate output information. The output information is applied to one or more output devices. In some embodiments, the communication interface may be a network communication interface. In embodiments in which elements may be combined, the communication interface may be a software communication interface, such as those for inter-process communication. In still other embodiments, there may be a combination of communication interfaces implemented as hardware, software, and combination thereof.

Throughout the discussion, numerous references will be made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

Various example embodiments are described herein. Although each embodiment represents a single combination of inventive elements, all possible combinations of the disclosed elements include the inventive subject matter. Thus if one embodiment comprises elements A, B, and C, and a second embodiment comprises elements B and D, then the inventive subject matter is also considered to include other remaining combinations of A, B, C, or D, even if not explicitly disclosed.

The term "connected" or "coupled to" may include both direct coupling (in which two elements that are coupled to each other contact each other) and indirect coupling (in which at least one additional element is located between the two elements).

The technical solution of embodiments may be in the form of a software product. The software product may be stored in a non-volatile or non-transitory storage medium, which can be a compact disk read-only memory (CD-ROM), a USB flash disk, or a removable hard disk. The software product includes a number of instructions that enable a computer device (personal computer, server, or network device) to execute the methods provided by the embodiments.

The embodiments described herein are implemented by physical computer hardware, including computing devices, servers, receivers, transmitters, processors, memory, displays, and networks. The embodiments described herein provide useful physical machines and particularly configured computer hardware arrangements. The embodiments described herein are directed to electronic machines and methods implemented by electronic machines adapted for processing and transforming electromagnetic signals which represent various types of information.

Figure 14:
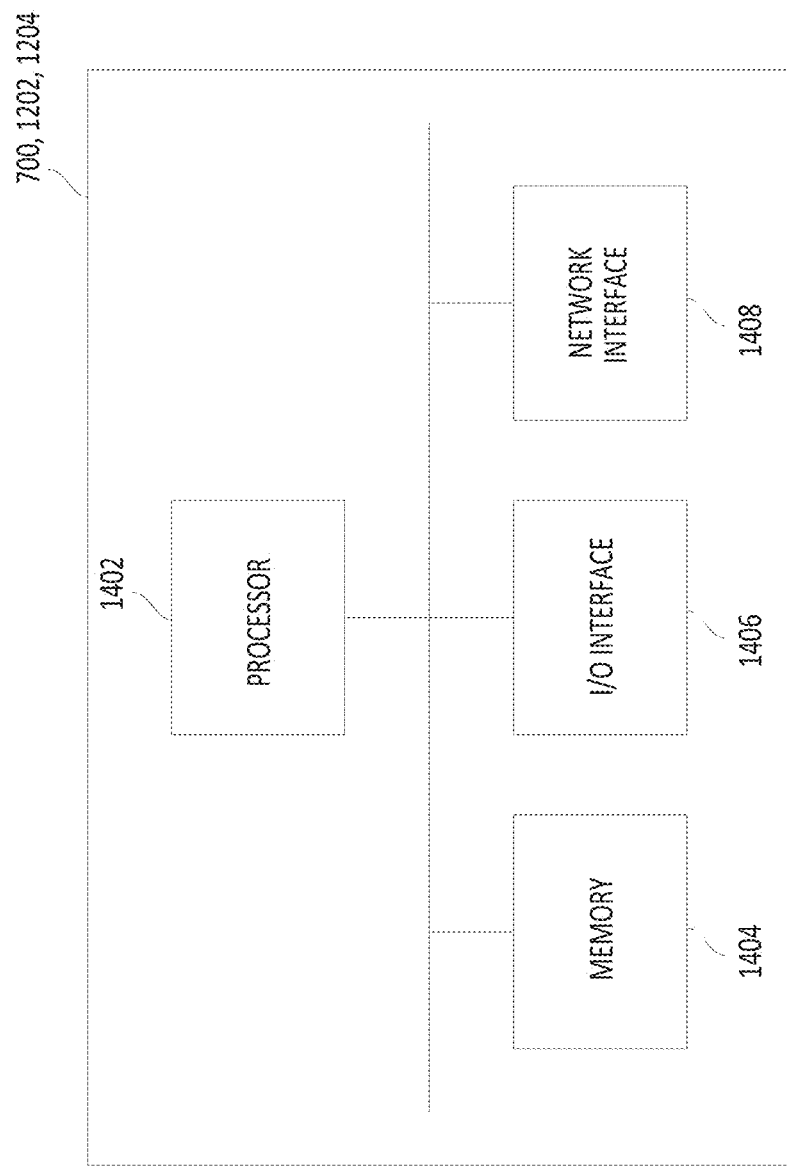
FIG. 14 is a schematic diagram of computing device that implements aspects of a healthcare system according to some embodiments.

FIG. 14 is a schematic diagram of healthcare system 700, exemplary of an embodiment. As depicted, healthcare system 700 includes at least one processor 1402, memory 1404, at least one I/O interface 1406, and at least one network interface 1408. The computing device components may be connected in various ways including directly coupled, indirectly coupled via a network, and distributed over a wide geographic area and connected via a network (which may be referred to as "cloud computing").

Each processor 1402 may be, for example, any type of general-purpose microprocessor or microcontroller, a digital signal processing (DSP) processor, an integrated circuit, a field programmable gate array (FPGA), a reconfigurable processor, or any combination thereof.

Memory 1404 may include a suitable combination of any type of computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like.

Each I/O interface 1406 enables healthcare system 700 to interconnect with one or more input devices, such as a keyboard, mouse, camera, touch screen and a microphone, or with one or more output devices such as a display screen and a speaker.

Each network interface 1408 enables healthcare system 700 to communicate with other components, to exchange data with other components, to access and connect to network resources, to serve applications, and perform other computing applications by connecting to a network (or multiple networks) capable of carrying data.

Healthcare system 700 is operable to register and authenticate users (using a login, unique identifier, and password for example) prior to providing access to applications, a local network, network resources, other networks and network security devices. Healthcare system 700 may server multiple users.

Although the embodiments have been described in detail, it should be understood that various changes, substitutions and alterations can be made herein without departing from the scope as defined by the appended claims.

Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed, that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A computer-implemented method for returning one or more unique identifiers identifying users or equipment in a medical environment whose characteristics satisfy one or more search criteria, the method comprising:

receiving, at an input interface of a hardware processor, an expression string including one or more lexical constraints representative of the one or more search criteria, each of the one or more lexical constraints provided in an order in the string, where the order is defined by one or more section constraints of a first external domain-specific query language;

parsing the expression string to extract one or more substrings from the expression string by grouping at least one of lexical constraints, words, numbers, or lists with no more than two lexical tokens, words, numbers or lists adjacent to only one other lexical token, word, number or list identified as belonging to another section, each substring representing a corresponding section within the expression string;

for each substring, classifying the substring to determine a corresponding programmatic query filter type and extracting one or more programmatic query filter parameters by parsing the substring based on a reference filter parameter syntax;

for each substring, instantiating the corresponding programmatic query filter based at least on the one or more filter parameters to generate one or more internal domain-specific language query strings representative of the programmatic query filter, and executing the one or more internal domain-specific language query strings to conduct query operations on one or more data stores housing multi-dimensional data sets associated with the users or the equipment to return a set of user or equipment unique identifiers that match the one or more filter parameters;

combining the returned sets of user or equipment unique identifiers from each of the instantiated programmatic query filters to identify a subset of users or equipment that satisfy the one or more search criteria; and returning an output data structure storing the one or more unique identifiers identifying the users or the equipment in the medical environment whose characteristics satisfy the one or more search criteria.

2. The method of claim 1, wherein instantiating the corresponding programmatic query filter further includes automatically determining one or more selected internal domain-specific languages from a plurality of available internal domain-specific languages, and the plurality of available internal domain-specific languages includes at least a declarative set-based query language and a procedural query language.

3. The method of claim 2, wherein instantiating the corresponding programmatic query filter includes generating at least a first internal domain-specific language query string and at a second internal domain-specific language query string that are cascaded in operation relative to one another, the first internal domain-specific language query string conducted in a first internal domain-specific language, and the second internal domain-language query string conducted in a second internal domain-specific language;

wherein the first internal domain-specific language is different than the second internal domain-specific language.

4. The method of claim 2, wherein the first internal domain-specific language is a declarative set-based query language, and the second internal domain-specific language is a procedural query language.

5. The method of claim 4, wherein the step of executing the one or more internal domain-specific language query strings includes:

executing the first internal domain-specific language query string against the multi-dimensional data sets, loading only the multi-dimensional data sets associated with identifiers identified by the execution of the first internal domain-specific language query string into a short-term data structure; and executing the second internal domain-specific language query string against the multi-dimensional data sets loaded into the short-term data structure.

6. The method of claim 1, further comprising:
processing the output data structure to automatically update, for each of the one or more unique identifiers, a corresponding Boolean flag representative of an alert notification associated with the users or the equipment corresponding to the one or more unique identifiers, the corresponding Boolean flag indicating that the users or the equipment had been identified as a result of processing the expression string.

7. The method of claim 6, further comprising appending, for each identifier in the output data structure, on the one or more data stores in data records associated with the users or the equipment, one or more hash strings generated from a current state of the multi-dimensional data sets associated with the users or the equipment corresponding to the identifier in the output data structure.

8. The method of claim 7, wherein the processing the output data structure to automatically update the corresponding Boolean flag representative of an alert notification occurs only upon a determination that the generated hash string corresponding to the identifier is different than a prior hash string stored in the one or more data stores associated with the user or the equipment corresponding to the identifier.

9. The method of claim 1, wherein the each substring and its corresponding instantiated programmatic query filters are executed sequentially in accordance with the order of the one or more lexical constraints;
and wherein the parsing of the expression string to extract the one or more substrings from the expression string is conducted by sequentially processing characters of the expression string from a start end to a finish end of the expression string, each programmatic query filter being instantiated and executed responsive to a parser traversing to a character representing the end of a substring.

10. The method of claim 1, wherein there is a 1:1 mapping between the one or more substrings and the one or more internal domain-specific language query strings.

11. A computer-implemented system for returning one or more unique identifiers identifying users or equipment in a medical environment whose characteristics satisfy one or more search criteria, the system comprising:
a processor coupled to computer memory storing machine-interpretable instructions, which when executed, cause the processor to perform a method comprising:
receiving, at an input interface an expression string including one or more lexical constraints representative of the one or more search criteria, each of the one or more lexical constraints in an order in the string, where the order is defined by one or more section constraints of a first external domain-specific query language;
parsing the expression string to extract one or more substrings from the expression string by grouping at least one of lexical constraints, words, numbers, or lists with no more than two lexical tokens, words, numbers or lists adjacent to only one other lexical token, word, number or list identified as belonging to another section, each substring representing a corresponding section within the expression string;
for each substring, classifying the substring to determine a corresponding programmatic query filter type and extracting one or more programmatic query filter parameters by parsing the substring based on a reference filter parameter syntax;
for each substring, instantiating the corresponding programmatic query filter based at least on the one or more filter parameters to generate one or more internal domain-specific language query strings representative of the programmatic query filter, the filter instantiation engine further configured to execute the one or more internal domain-specific language query strings to conduct query operations on one or more data stores housing multi-dimensional data sets associated with the users or the equipment to return a set of user or equipment unique identifiers that match the one or more filter parameters;
combining the returned sets of user or equipment unique identifiers from each of the instantiated programmatic query filters to identify a subset of users or equipment that satisfy the one or more search criteria; and
returning an output data structure storing the one or more unique identifiers identifying the users or the equipment in the medical environment whose characteristics satisfy the one or more search criteria.

12. The system of claim 11, wherein instantiating the corresponding programmatic query filter further includes automatically determining one or more selected internal domain-specific languages from a plurality of available internal domain-specific languages, and the plurality of available internal domain-specific languages includes at least a declarative set-based query language and a procedural query language.

13. The system of claim 12, wherein the method further comprises generating at least a first internal domain-specific language query string and at a second internal domain-specific language query string that are cascaded in execution relative to one another, the first internal domain-specific language query string conducted in a first internal domain-specific language, and the second internal domain-language query string conducted in a second internal domain-specific language;
wherein the first internal domain-specific language is different than the second internal domain-specific language.

14. The system of claim 12, wherein the first internal domain-specific language is a declarative set-based query language, and the second internal domain-specific language is a procedural query language.

15. The system of claim 14, wherein the execution the one or more internal domain-specific language query strings includes:
executing the first internal domain-specific language query string against the multi-dimensional data sets,
loading only the multi-dimensional data sets associated with identifiers identified by the execution of the first internal domain-specific language query string into a short-term data structure; and
executing the second internal domain-specific language query string against the multi-dimensional data sets loaded into the short-term data structure.

16. The system of claim 11, wherein the method further comprises processing the output data structure to automatically update, for each of the one or more unique identifiers, a corresponding Boolean flag representative of an alert notification associated with the users or the equipment corresponding to the one or more unique identifiers, the corresponding Boolean flag indicating that the users or the equipment had been identified as a result of processing the expression string.

17. The system of claim 16, further comprising appending, for each identifier in the output data structure, on the one or more data stores in data records associated with the users or the equipment, one or more hash strings generated from a current state of the multi-dimensional data sets associated with the users or the equipment corresponding to the identifier in the output data structure.

18. The system of claim 17, wherein the processing the output data structure to automatically update the corresponding Boolean flag representative of an alert notification occurs only upon a determination that the generated hash string corresponding to the identifier is different than a prior hash string stored in the one or more data stores associated with the user or the equipment corresponding to the identifier.

19. The system of claim 11, wherein the each substring and its corresponding instantiated programmatic query filters are executed sequentially in accordance with the order of the one or more lexical constraints;

and wherein the parsing of the expression string to extract the one or more substrings from the expression string is conducted by sequentially processing characters of the expression string from a start end to a finish end of the expression string, each programmatic query filter being instantiated and executed responsive to a parser traversing to a character representing the end of a substring.

20. A non-transitory computer-readable medium storing machine-interpretable instructions, which when executed by a processor, cause the processor to perform a method for returning one or more unique identifiers identifying users or equipment in a medical environment whose characteristics satisfy one or more search criteria, the method comprising:
receiving, at an input interface of a hardware processor, an expression string including one or more lexical constraints representative of the one or more search criteria, each of the one or more lexical constraints in an order in the string, where the order is defined by one or more section constraints of a first external domain-specific query language;
parsing the expression string to extract one or more substrings from the expression string by grouping at least one of lexical constraints, words, numbers, or lists with no more than two lexical tokens, words, numbers or lists adjacent to only one other lexical token, word, number or list identified as belonging to another section, each substring representing a corresponding section within the expression string;
for each substring, classifying the substring to determine a corresponding programmatic query filter type and extracting one or more programmatic query filter parameters by parsing the substring based on a reference filter parameter syntax;
for each substring, instantiating the corresponding programmatic query filter based at least on the one or more filter parameters to generate one or more internal domain-specific language query strings representative of the programmatic query filter, and executing the one or more internal domain-specific language query strings to conduct query operations on one or more data stores housing multi-dimensional data sets associated with the users or the equipment to return a set of user or equipment unique identifiers that match the one or more filter parameters;
combining the returned sets of user or equipment unique identifiers from each of the instantiated programmatic query filters to identify a subset of users or equipment that satisfy the one or more search criteria; and
returning an output data structure storing the one or more unique identifiers identifying the users or the equipment in the medical environment whose characteristics satisfy the one or more search criteria.

* * * * *